(12) United States Patent
Bryant et al.

(10) Patent No.: US 6,599,920 B2
(45) Date of Patent: Jul. 29, 2003

(54) NAPHTHALENE COMPOUNDS, INTERMEDIATES, FORMULATIONS, AND METHODS

(75) Inventors: Henry Uhlman Bryant, Indianapolis, IN (US); Thomas Alan Crowell, Indianapolis, IN (US); Charles David Jones, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/918,967

(22) Filed: Aug. 26, 1997

(65) Prior Publication Data

US 2003/0100754 A1 May 29, 2003

Related U.S. Application Data

(60) Provisional application No. 60/025,127, filed on Aug. 29, 1996.

(51) Int. Cl.$^7$ ..................... A61K 31/445; C07D 211/06
(52) U.S. Cl. ................. 514/319; 514/212; 514/238.8; 514/428; 514/609; 514/651; 540/609; 544/106; 546/205; 548/576; 564/347
(58) Field of Search ............ 540/609; 544/106; 546/205; 548/576; 564/347; 514/212, 238.8, 319, 428, 609, 651

(56) References Cited

U.S. PATENT DOCUMENTS

| | | | | |
|---|---|---|---|---|
| 3,394,125 A | | 7/1968 | Crenshaw | 548/525 |
| 3,413,305 A | | 11/1968 | Crenshaw | 548/525 |
| 3,506,653 A | * | 4/1970 | Fried | 548/523 |
| 4,133,814 A | | 1/1979 | Jones et al. | 548/525 |
| 4,230,862 A | | 10/1980 | Suarez et al. | 546/237 |
| 4,358,593 A | | 11/1982 | Jones et al. | 546/202 |
| 4,380,635 A | | 4/1983 | Peters | 546/202 |
| 4,418,068 A | | 11/1983 | Jones et al. | 546/237 |
| 5,395,842 A | | 3/1995 | Labrie et al. | 514/320 |
| 5,470,854 A | | 11/1995 | Angerer et al. | 514/233 |
| 5,472,962 A | | 12/1995 | Koizumi et al. | 514/233.5 |
| 5,484,795 A | * | 1/1996 | Bryant et al. | 514/319 |

FOREIGN PATENT DOCUMENTS

| | | |
|---|---|---|
| EP | 062 503 | 10/1982 |
| WO | WO 89/0289 | 4/1989 |
| WO | WO 95/10513 | 4/1995 |

OTHER PUBLICATIONS

Grese et al. "Structure activity relationship of selective estrogen receptor . . . " J. Med. Chem. v. 40, p. 146–167 (1997).*
Mittal et al. "Structure–activity relationship of estrogens: receptor affinity and estrogen antagonist activity . . . " J. Med. chem. v. 28, p. 492–497, 1985.*
Bradley et al. "Thermolysis of 2–benzylidenebenzocyclcobutanols" CA 117:233209, 1992.*
Ruenitz et al., J. Med. Chem., 25:1056–1060 (1982).
Jordan et al., Molecular Pharmacology, 26:272–278 (1984).
Foster et al., J. Med. Chem., 28:1491–1497 (1985).
Loser et al., Eur. J. Cancer Clin. Oncol., 21:985–990 (1985).
Crenshaw, R.R., et al, *J. Med. Chem.* 14(12):1185–1190 (1971).
Jones, C.D., et al, *J. Med. Chem.* 27: 1057–1066) 1984.
Jones, C.D., et al, *J. Med. Chem.* 35: 931–938 1992.

\* cited by examiner

*Primary Examiner*—Ceila Chang
(74) *Attorney, Agent, or Firm*—Gary M. Birch; Gilbert T. Voy

(57) ABSTRACT

This invention relates to the field of pharmaceutical and organic chemistry and provides naphthalene compounds, intermediates, formulations, and methods.

17 Claims, No Drawings

NAPHTHALENE COMPOUNDS, INTERMEDIATES, FORMULATIONS, AND METHODS

This application claims the benefit of U.S. Provisional Application No. 60/025,127 filed Aug. 29, 1996.

BACKGROUND OF THE INVENTION

This invention relates to the field of pharmaceutical and organic chemistry and provides naphthalene compounds, intermediates, formulations, and methods.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosomax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Another major estrogen associated pathology is estrogen-dependent breast cancer and, to a lesser extent, estrogen-dependent cancers of other organs, particularly the uterus. Although such neoplasms are not solely limited to a postmenopausal woman, they are more prevalent in the older, postmenopausal population. Current chemotherapy of these cancers have relied heavily on the use of anti-estrogen compounds, such as tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be counterproductive in some cases. A better therapy for the treatment of these cancers would be an agent which is an antiestrogenic compound having fewer or no estrogen agonist properties on reproductive tissues.

Thus, it would be a significant contribution to the art to provide novel compounds useful, for example, in the treatment or prevention of the disease states as indicated herein.

SUMMARY OF THE INVENTION

The present invention relates to compounds of formula I

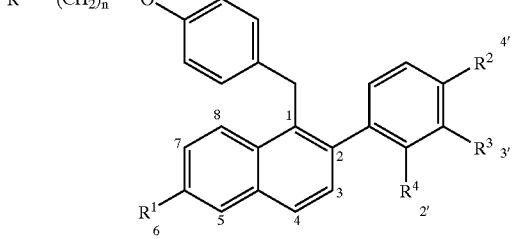

wherein $R^1$ is —H, —OH, —O($C_1$-$C_4$ alkyl), —OCO($C_1$-$C_6$ alkyl), —O—CO—O($C_1$-$C_6$ alkyl), —O—CO—Ar, —OSO$_2$($C_2$-$C_6$ alkyl), —O—CO—OAr, where Ar is optionally substituted phenyl;

$R^2$ is —H, —Cl, —F, $C_1$-$C_4$ alkyl, —OH, —O($C_1$-$C_4$ alkyl), —OCO($C_1$-$C_6$ alkyl), —O—CO—O($C_1$-$C_6$ alkyl), —O—CO—Ar, —OSO$_2$($C_2$-$C_6$ alkyl), or —O—CO—OAr, where Ar is optionally substituted phenyl;

$R^3$ and $R^4$ are, independently, $R^2$, with the proviso that $R^3$ and $R^4$ are not both hydrogen.

$R^5$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino; and n is 2 or 3;

or a pharmaceutically acceptable salt or solvate thereof.

DETAILED DESCRIPTION OF THE INVENTION

The present invention further relates to intermediate compounds of formula II which are useful for preparing the pharmaceutically active compounds of the present invention, and are shown below:

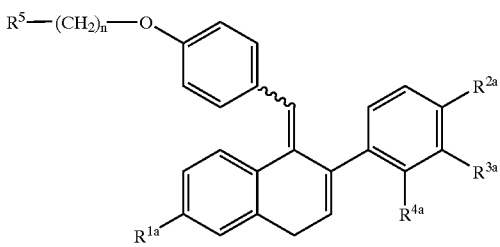

II wherein
 $R^{1a}$ is —H or —$OR^6$ in which $R^6$ is a hydroxy protecting group;
 $R^{2a}$, $R^{3a}$, and $R^{4a}$ are, independently, —H, —Cl, —F, $C_1$–$C_4$ alkyl, —$OR^6$ in which $R^6$ is a hydroxy protecting group;
 n and $R^5$ have their previous meanings;
 and further, wherein said compound is in the Z— or E— stereoisomeric form, and mixtures thereof.

Further, the present invention provides intermediate compounds of formula III which are useful for preparing the pharmaceutically active compounds of the present invention, and are shown below.

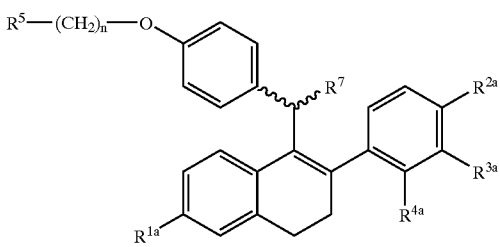

III wherein
 $R^{1a}$, $R^{2a}$, $R^{3a}$, $R^{4a}$, $R^5$, and n have their previous meanings and provisions; and
 $R^7$ is —OH or —$OR^8$, where $R^8$ is a $C_1$–$C_6$ alkyl sulfonyl or aryl sulfonyl.

The present invention further provides intermediate compounds of formula IX which are useful for preparing the pharmaceutically active compounds of the present invention, and are shown below:

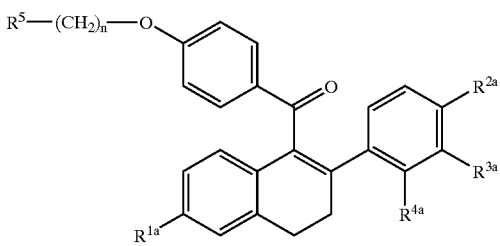

IX wherein:
 $R^{1a}$, $R^{2a}$, $R^{3a}$, $R^{4a}$, $R^5$, and n have their previous meanings and provisions.

The present invention further relates to pharmaceutical compositions containing compounds of formula I.

Still further, the current invention provides methods for the therapeutic use of such compounds and compositions.

General terms used in the description of compounds herein described bear their usual meanings. For example, "$C_1$–$C_6$ alkyl" refers to straight or branched aliphatic chains of 1 to 6 carbon atoms including moieties such as methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen molecule and include moieties such as, for example, methoxy, ethoxy, n-propoxy, isopropoxy, and the like. Of these alkoxy groups, methoxy is highly preferred in most circumstances.

Optionally substituted phenyl includes phenyl and phenyl substituted once or twice with $C_1$–$C_6$ alkyl, $C_1$–$C_4$ alkoxy, hydroxy, nitro, chloro, fluoro, or tri (chloro or fluoro)methyl.

The term, "hydroxy protecting group" contemplates numerous functionalities used in the literature to protect a hydroxyl function during a chemical sequence and which can be removed to yield the phenol. Included within this group would be acyls, mesylates, tosylates, benzyl, alkylsilyloxys, —$OC_1$–$C_4$ alkyls, and the like. Numerous reactions for the formation and removal of such protecting groups are described in a number of standard works including, for example, Protective Groups in Organic Chemistry, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred $R^6$ hydroxy protecting groups, particularly methyl, are essentially as described in Example 2, infra.

The term "inhibit" includes its generally accepted meaning which includes prohibiting, preventing, restraining, alleviating, ameliorating, and slowing, stopping or reversing progression, severity, or a resultant symptom. As such, the present method includes both medical therapeutic and/or prophylactic administration, as appropriate.

The starting material for preparing compounds of the present invention is a compound of formula IV

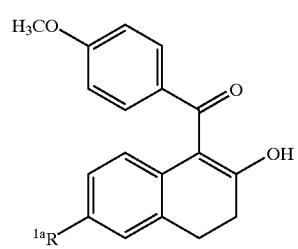

IV wherein
 $R^{1a}$ is —H or —$OR^6$ in which $R^6$ is a hydroxy protecting group, preferred is methyl.

Compounds of formula IV are known in the art and are prepared essentially as described by Jones et al., in U.S. Pat. No. 4,400,543 and Jones et al., in U.S. Pat. No. 5,147,880 each of which are herein incorporated by reference. See, also, Jones et al., *J. Med. Chem.*, 35:931–8 (1992) and Jones et al., *J. Med. Chem.*, 22:962 (1979).

In preparing compounds of the present invention, generally, a 1-acylated-2-tetralone of formula IV (written in its enolic form) is treated with a base to form its corresponding anion, which is reacted with diphenylchlorophosphate, providing an enol phosphate derivative of formula V. The formula V compound undergoes formal addition-elimination when treated with an aryl Grignard reagent (VI), which results in substitution of the 2-phosphate substituent by the aryl moiety, thereby producing a compound of formula VII. Dealkylation of a formula VII compound by a thiolate anion demethylation reagent selectively dealkylates the group which is located para to the electron-withdrawing carbonyl group. The result of such selective dealkylation is a phenolic compound of formula VII', which serves as an intermediate to the compounds of this invention. This synthetic route is as shown below in Scheme I, and $R^{1a}$, $R^{2a}$, $R^{3a}$, and $R^{4a}$ have their previous meanings and provisions.

equivalents of an aryl Grignard reagent or an aryl lithium organocuprate reagent. One to two equivalents of an aryl magnesium bromide (VI) is preferred. Such Grignard reagents would include, but are not limited to: 3-methoxyphenyl magnesium bromide, 3-chlorophenyl magnesium bromide, 2-methoxyphenyl magnesium bromide, 3-fluorophenyl magnesium bromide, 3-methylphenyl magnesium bromide, 2-methylphenyl magnesium bromide, 2-methyl-3-methoxyphenyl magnesium

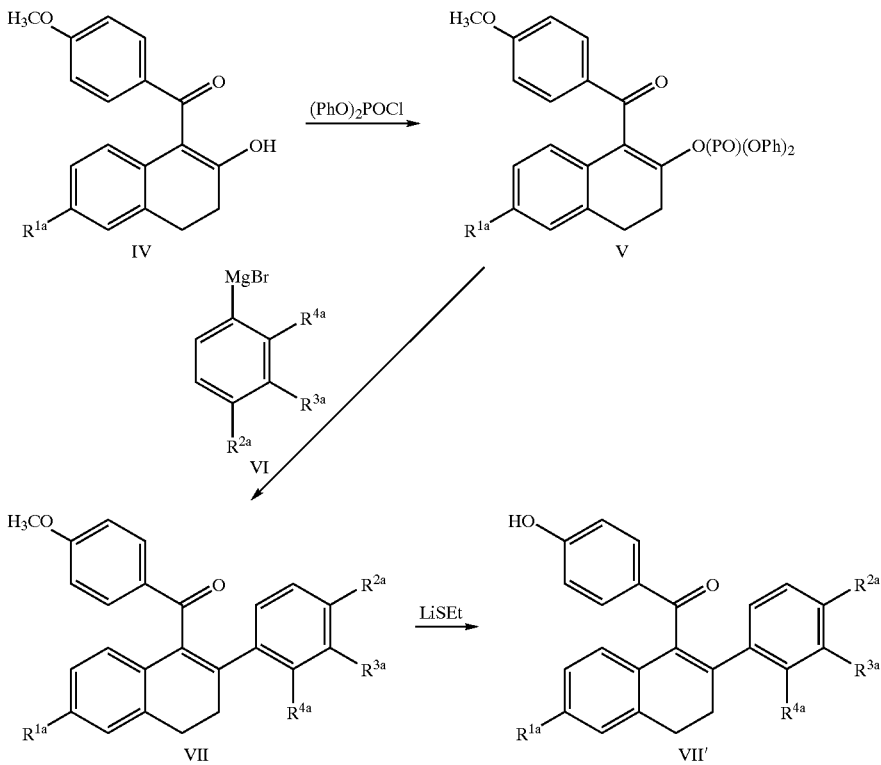

In particular, a formula IV enolic compound is phosphorylated by one or more equivalents of a phosphorylating reagent which is a diarylchloro- or diarylbromo-phosphate and preferably diphenylchlorophosphate. This reaction, may be carried out in a variety of inert solvents including ethers, THF, dioxane, ethyl acetate, toluene, and acetonitrile and in the presence of a strong base such as an alkali metal hydride, alkali metal hydroxide, or alkali metal carbonate or a trialkyl amine such as triethyl amine. The alkali metal base or tertiary amine acts as a basic catalyst in the phosphorylation process. Although it is preferable to run the reaction at ice bath temperature so as to avoid unwanted side products, elevated temperatures can also be used, but they are usually unnecessary to complete the phosphorylation reaction. The product of the phosphorylation reaction, an enol phosphate derivative of formula V may be isolated by usual techniques, such as chromatography. However, it is most convenient to generate the enolphosphate using a solvent/acid scavenger combination which is compatable with the next step of the reaction (additon of a Grignard Reagent). Thus, the combination of sodium hydride in THF under a nitrogen atmosphere is preferred, and leads to a rapid phosphorylation providing a compound of formula V.

The intermediate enol phosphate (V), either isolated or generated in situ, may then be reacted with one or more bromide, 3-methoxy-4-fluorophenyl magnesium bromide, 2-chloro-4-methoxyphenyl magnesium bromide, 3,4-dimethoxyphenyl magnesium bromide, 3-fluoro-4-methoxyphenyl magnesium bromide, and the like. The reaction is typically conducted at ice bath temperatures to minimize side reactions, but elevated temperatures can be used to increase the rate of the reaction. The addition of the aryl moiety, followed by the elimination of the phosphate leaving group (formally a 1,4-addition, elimination process) gives rise to a dihydronaphthalene derivative of formula VII, which may then be isolated by conventional techniques such as crystallization or chromatography.

The resulting dihydronaphthalene derivative of formula VII is then demethylated to provide an intermediate of formula VII' which completes the chemical sequence as shown in Scheme I. In order to accomplish regioselective demethylation at the methoxy group para to the carbonyl, a nucleophilic demethylation reagent is used, and alkali metal thiolates (alkali metal salt of an organic thiol) are preferred. Especially preferred are lithium thioethylate or lithium thiomethylate, in excess to the extent of 1.2 or more equivalents of the demethylation reagent over the substrate. The reaction is conducted under an inert atmosphere to preserve the demethylation reagent and in a solvent which is practically inert to the nucleophilic nature of the thiolate reagent.

Suitable solvents for the demethylation are those which are most conducive to bimolecular nucleophilic displacement reactions, and these include dimethylsulfoxide dimethylformamide, dimethylacetamide, and THF. Anhydrous dimethylformamide is preferred. In order to simultaneously achieve a satisfactory reaction rate and also obtain good control of the selectivity for demethylation at the site para to the carbonyl group, it is important to carefully control the temperature of the reaction. Although the demethylation process will take place in the range of temperatures from 60° C. to 120° C., it is advantageous to use a temperature in the range of 80°–90° C. to optimize the yield of the desired product. A temperature of 80° C. is particularly preferred. Under the preferred reaction conditions, the transformation from a formula VII compound to a formula VII' compound is complete after heating for about 2 to 4 hours at the indicated temperature.

Compounds of formula VII and VII' collectively are novel intermediates which are useful for the preparation of pharmaceutically active compounds of formula I of the present invention. Compounds of formula VII and VII' would include, but not be limited to:

[2-(3-methoxyphenyl)-3,4-dihydro-6-methoxynaphthalen-1-yl][4-methoxyphenyl]methanone

[2-(3-methoxyphenyl)-3,4-dihydro-6-methoxynaphthalen-1-yl][4-hydroxyphenyl]methanone

[2-(3-methoxyphenyl)-3,4-dihydro-naphthalen-1-yl][4-methoxyphenyl]methanone

[2-(3-methoxy-4-methylphenyl)-3,4-dihydro-naphthalen-1-yl][4-hydroxyphenyl]methanone

[2-(2-methoxyphenyl)-3,4-dihydro-6-methoxynaphthalen-1-yl][4-methoxyphenyl]methanone

[2-(3,4-di-methoxyphenyl)-3,4-dihydro-6-methoxynaphthalen-1-yl][4-methoxyphenyl]methanone

[2-(3,4-di-methoxyphenyl)-3,4-dihydro-6-methoxynaphthalen-1-yl][4-hydroxyphenyl]methanone

[2-(3-chlorophenyl)-3,4-dihydro-6-methoxynaphthalen-1-yl][4-methoxyphenyl]methanone

[2-(2-methoxy-3-fluorophenyl)-3,4-dihydro-6-methoxynaphthalen-1-yl][4-methoxyphenyl]methanone

[2-(2-methyl-2-methyl-3-methoxyphenyl)-3,4-dihydro-6-methoxynaphthalen-1-yl][4-hydroxyphenyl]methanone

[2-(3-methoxy-4-fluorophenyl)-3,4-dihydro-naphthalen-1-yl][4-methoxyphenyl]methanone

[2-(2-chloro-3-methoxyphenyl)-3,4-dihydro-6-methoxynaphthalen-1-yl][4-hydroxyphenyl]methanone

[2-(2-ethyl-4-methoxyphenyl)-3,4-dihydro-6-methoxynaphthalen-1-yl][4-hydroxyphenyl]methanone

[2-(2,4-dimethyl-3-methoxyphenyl)-3,4-dihydro-naphthalen-1-yl][4-methoxyphenyl]methanone

[2-(2-chloro-3-methoxy-4-fluorophenyl)-3,4-dihydro-6-methoxynaphthalen-1-yl][4-hydroxyphenyl]methanone Upon preparation of a formula VII' compound, it is reacted with a compound of formula VIII

wherein $R^5$ and n are as defined above and Q is a bromo or, preferably, a chloro moiety, or a salt thereof, to form a compound of formula IX'. The formula IX' compound may be deprotected, when $R^6$ hydroxy protecting groups are present, to form a compound of formula IX". These process steps are shown in Scheme III below.

Scheme II

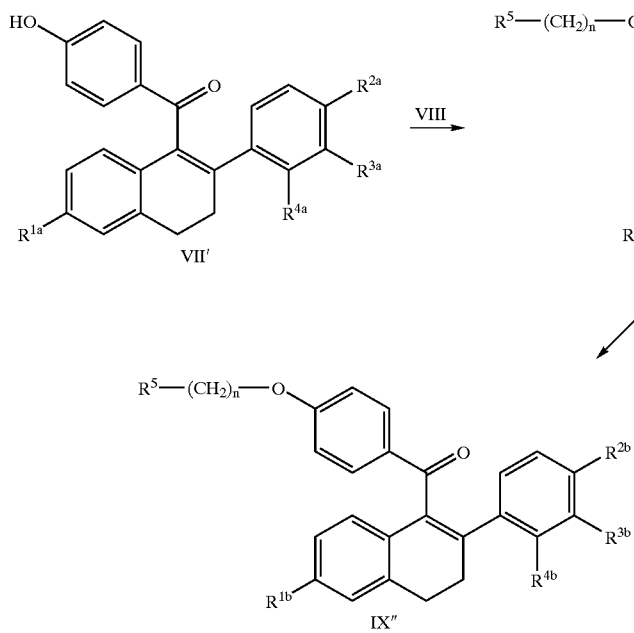

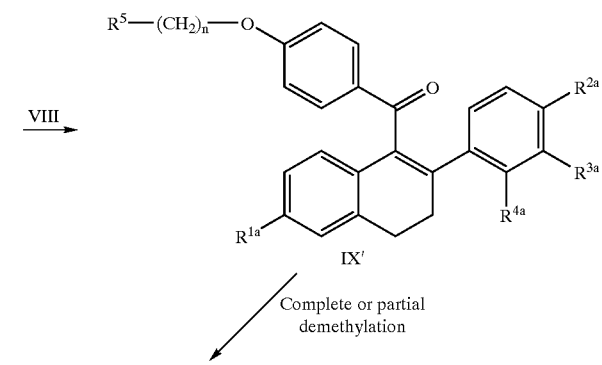

wherein
  $R^{1a-4a}$, n, and $R^5$ have their previous meanings and provisions;
  $R^{1b}$ is —H, —OH, or —OCH$_3$;
  $R^{2b}$, $R^{3b}$, and $R^{4b}$ are, independently, —H, —Cl, —F, —OH, —OCH$_3$, or C$_1$–C$_4$ alkyl, with the proviso that $R^{3b}$ and $R^{4b}$ are not both hydrogen;
  or a pharmaceutically acceptable salt or solvate thereof.

In the first step of the process shown in Scheme II, the alkylation is carried out via standard procedures. Compounds of formula VIII are commercially available or are prepared by means well known to one of ordinary skill in the art. Compounds of formula VIII would include, but not be limitd to: 1-(2-chloroethyl)piperidine hydrochloride, 1-(2-chloroethyl)pyrrolidine hydrochloride, 1-(2-chloroethyl) hexamethyleneimino hydrochloride, 1-(3-chloropropyl) piperidine hydrochloride, 1-(3-chloropropyl)-2-methylpyrrolidine hydrochloride, 2-chloroethyl-N,N-dimethylamine hydrochloride, 3-chloro-N,N-diethylamine hydrochloride, 1-(2-chloroethyl)piperidine, 1-(2-chloroethyl)-3,3-dimethylpyrrolidine hydrochloride, 1-(2-chloroethyl)-3-methylpyrrolidine hydrochloride, 1-(3-chloropropyl)piperidine hydrochloride, 1-(3-chloropropyl) hexamethyleneimino hydrochloride, and the like. Preferably, the hydrochloride salt of a formula VIII compound, particularly 2-chloroethylpiperidine hydrochloride, is used.

Generally, one equivalent of formula VII' substrate is reacted with 2 equivalents of a formula VIII compound in the presence of at least about 4 equivalents of an alkali metal carbonate, preferably cesium carbonate or potassium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Often, ambient temperature is sufficient and preferred, but in certain cases, higher temperatures may be required.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative for preparing compounds of formulae IX' or IX'', a formula VII' compound is reacted with an excess of an alkylating agent of the formula

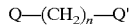

wherein Q and Q' each are the same or different leaving group and n is two or three, in an alkali solution. This sequence is illustrated in the first reaction in Scheme III, below. Appropriate leaving groups include the sulfonates such as methanesulfonate, 4-bromobenzenesulfonate, toluenesulfonate, ethanesulfonate, isopropylsulfonate, 4-methoxybenzenesulfonate, 4-nitrobenzenesulfonate, 2-chlorobenzenesulfonate, triflate, and the like, halogens such as bromo, chloro, and iodo, and other related leaving groups. Halogens are preferred leaving groups and bromo is especially preferred.

A preferred alkali solution for this alkylation reaction contains potassium carbonate in an inert solvent such as, for example, methylethyl ketone (MEK) or DMF. In this solution, the 4-hydroxy group of the benzoyl moiety of a formula VII' compound exists as a phenoxide ion which displaces one of the leaving groups of the alkylating agent.

This reaction is best when the alkali solution containing the reactants and reagents is brought to reflux and allowed to run to completion. When using MEK as the preferred solvent, reaction times run from about 6 hours to about 20 hours.

Scheme III

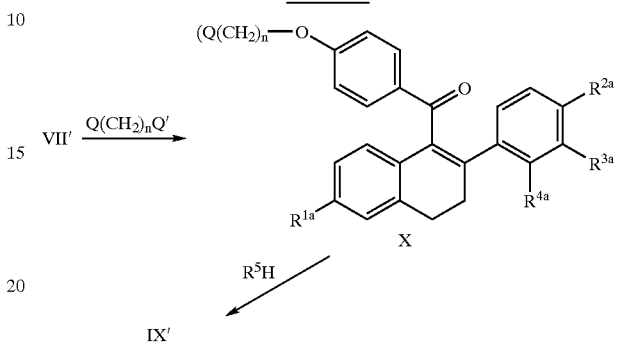

wherein:
  $R^{1a}$, $R^{2a}$, $R^{3a}$, $R^{4a}$, $R^5$, n, and Q have their previous meanings and provisions.

Compounds of formula X would include, but not be limited to:
  [2-(3-methoxyphenyl)-6-methoxy-3,4-dihydronaphthalene-1-yl][4-(2-bromoethoxy)phenyl] methanone
  [2-(2-methoxyphenyl)-6-methoxy-3,4-dihydronaphthalene-1-yl][4-(2-bromoethoxy)phenyl] methanone
  [2-(3-methoxyphenyl)-6-methoxy-3,4-dihydronaphthalene-1-yl][4-(3-bromopropoxy)phenyl] methanone
  [2-(3-methoxy-4-fluorophenyl)-6-methoxy-3,4-dihydronaphthalen-1-yl][4-(2-bromoethoxy)phenyl] methanone
  [2-(3-chlorophenyl)-6-methoxy-3,4-dihydronaphthalene-1-yl][4-(2-bromoethoxy)phenyl]methanone
  [2-(3-methyl-4-methoxyphenyl)-3,4-dihydronaphthalene-1-yl][4-(2-bromoethoxy)phenyl] methanone
  [2-(2-chloro-3-methoxyphenyl)-6-methoxy-3,4-dihydronaphthalene-1-yl][4-(2-bromoethoxy)phenyl] methanone, The reaction product from this step (X) is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, or other secondary amines ($R^5H$), via standard techniques, to form compounds of formula IX', as seen in the second reaction of Scheme III, supra. Preferably, the hydrochloride salt of piperidine is reacted with the alkylated compound of formula X in an inert solvent, such as anhydrous DMF, and heated to a temperature in the range of from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step may be monitored via standard chromatographic techniques.

An alternative route for preparing compounds of formula IX' is depicted in Scheme IV, below, wherein $R^{1a}$, $R^{2a}$, $R^{3a}$, $R^{4a}$, $R^5$, and n have their previous meanings and provisions.

Scheme IV

In this alternative, the starting material is a 1-acylated-2-tetralone of formula XI which already includes the basic side chain moiety. The compound of formula XI is treated with a base to form its corresponding anion, which is reacted with diphenylchlorophosphate, providing an enol phosphate derivative of formula XII. The compound of formula XII undergoes formal addition-elimination when treated with an aryl Grignard reagent (VI), which results in the substitution of the 2-phosphate substituent by the aryl moiety, thereby producing directly a formula IX' compound.

The compounds of formula XI may be prepared by the methods described in the references, infra. The further reactions outlined in Scheme IV are analogous to those described for Scheme I.

Compounds of formula IX" would include, but are not limited to.

[2-(3-methoxyphenyl)-3,4-dihydro-6-methoxynaphthalen-1-yl][4-[2-(1-piperidinyl)ethoxy]phenyl]methanone

[2-(3-methoxyphenyl)-3,4-dihydronaphthalen-1-yl][4-[2-(1-piperidinyl)ethoxy]phenyl]methanone

[2-(2-methoxyphenyl)-3,4-dihydro-6-methoxynaphthalen-1-yl][4-[2-(1-piperidinyl)ethoxy]phenyl]methanone

[2-(3-methoxyphenyl)3,4-dihydro-6-methoxynaphthalen-1-yl[]4-[2-(1-pyrolidinyl)ethoxy]phenyl]methanone

[2-(3-methoxyphenyl)3,4-dihydro-6-methoxynaphthalen-1-yl][4-[3-(1-piperidinyl)propoxy]phenyl]methanone

[2-(3-methoxy-4-fluorophenyl)-3,4-dihydro-6-methoxynaphthalen-1-yl][4-[2-(1-piperidinyl)ethoxy]phenyl]methanone

[2-(2-methyl-3-methoxyphenyl)-3,4-dihydro-6-methoxynaphthalen-1-yl][4-[2-(1-piperidinyl)ethoxy]phenyl]methanone

[2-(3-chloro-4-methoxyphenyl)-3,4-dihydro-6-methoxynaphthalen-1-yl][4-[2-(1-piperidinyl)ethoxy]phenyl]methanone

[2-(3-methoxyphenyl)-3,4-dihydro-6-methoxynaphthalen-1-yl][4-[2-(1-hexamethylenimino)ethoxy]phenyl]methanone

[2-(3,4-di-methoxyphenyl)-3,4-dihydro-6-methoxynaphthalen-1-yl][4-[2-(1-piperidinyl)ethoxy]phenyl]methanone Other preferred compounds of formula IX are obtained by cleaving, when present, the $R^6$ hydroxy protecting group of formula IX' compounds via well known procedures. Such procedures are cited in the references, supra. An exception to these general methods and involves those compounds of formula IX', wherein $R^{3a}$ bears an oxygen. In the case of these compounds, standard demethylating procedures, such as, the use of Lewis acids, for example, $BCl_3$, $AlCl_3$, $PBr_3$, and the like, leads to the formation of undesired by-products and the desired compounds (IX") can not be obtained. However, these compounds, wherein $R^3$ is hydroxy may be obtained by cleavage of the methoxy protecting group under basic conditions, such as LiSEt at −70° C.

Compounds of formula IX" would include, but are not limited to:

[2-(3-hydroxyphenyl)-3,4-dihydro-6-hydroxynaphthalen-1-yl][4-[2-(1-piperidinyl)ethoxy]phenyl]methanone

[2-(3-hydroxyphenyl)-3,4-dihydronaphthalen-1-yl][4-[2-(1-piperidinyl)ethoxy]phenyl]methanone

[2-(3-methoxyphenyl)-3,4-dihydro-6-hydroxynaphthalen-1-yl][4-[2-(1-piperidinyl)ethoxy]phenyl]methanone

[2-(3-hydroxyphenyl)-3,4-dihydro-6-methoxynaphthalen-1-yl][4-[2-(1-piperidinyl)ethoxy]phenyl]methanone

[2-(3-hydroxyphenyl)-3,4-dihydro-6-hydroxynaphthalen-1-yl][4-[2-(1-pyrolidinyl)ethoxy]phenyl]methanone

[2-(3-hydroxyphenyl)-3,4-dihydro-6-hydroxynaphthalen-1-yl][4-[3-(1-piperidinyl)propoxy]phenyl]methanone

[2-(2-hydroxyphenyl)-3,4-dihydro-6-hydroxynaphthalen-1-yl][4-[2-(1-piperidinyl)ethoxy]phenyl]methanone

[2-(3,4-di-hydroxyphenyl)-3,4-dihydro-6-hydroxynaphthalen-1-yl][4-[2-(1-piperidinyl)ethoxy]phenyl]methanone

[2-(3-hydroxy-4-chlorophenyl)-3,4-dihydro-6-hydroxynaphthalen-1-yl][4-[2-(1-piperidinyl)ethoxy]phenyl]methanone

[2-(2-fluoro-3-hydroxyphenyl)-3,4-dihydronaphthalen-1-yl][4-[2-(1-piperidinyl)ethoxy]phenyl]methanone and the like.

The compounds of formula IX' or IX" are the starting materials for the next series of reactions for the preparation of compounds of the current invention. In general, the compounds of formula IX' are most often employed, since any free phenols (IX") will consume extra reduction reagent.

The compounds of formula IX' may be converted to formula I compounds via two different reaction sequences. The choice of which sequence to use depends upon the $R^3$ substituent on the pendant phenyl ring. $IX^{b'}$ compounds, where $R^3$ has an oxygen function, for example, —OH, —OCH$_3$, and the like, may only be converted to formula I compounds by the second reaction sequence (Scheme VI), below. All other $IX^{a'}$ compounds, wherein $R^3$ is not an oxygen-bearing fuction, may be converted by either sequence, for example, Scheme V or VI.

The first step in both of the above-mentioned synthetic pathways (Scheme V and VI) is the reduction of the bridging carbonyl of the benzoyl moiety to the secondary alcohol (a compound of formula III$^a$, wherein $R^7$ is hydroxy). This reduction may be accomplished in a manner similar to that exemplified in U.S. Pat. No. 5,484,795, the disclosure of which is herein incorporated by reference. Briefly, a compound of formula IX is reduced with a hydride reagent, for example, LiAlH$_4$, NaBH$_4$, DIBAL, and the like, in an inert solvent such as ether, THF, toluene, and the like. Such reactions may be carried out at a variety of temperatures from –50 to 50° C., generally 0° C. to ambient temperature is most convenient and the reaction is complete within two to eighteen hours. This first step yields the compounds of formula III$^a$, which are intermediates for the preparation of the compounds formula I, and are useful for the pharmacologic methods of the current invention. Compounds of formula III$^a$, would include, but are not limited to:

[2-(3-methoxyphenyl)-3,4-dihydro-6-methoxynaphthalen-1-yl][4-[2-(1-piperidinyl)ethoxy]phenyl]methanol

[2-(3-methoxyphenyl)-3,4-dihydronaphthalen-1-yl][4-[2-(1-piperidinyl)ethoxy]phenyl]methanol

[2-(2-methoxyphenyl)-3,4-dihydro-6-methoxynaphthalen-1-yl][4-[2-(1-piperidinyl)ethoxy]phenyl]methanol

[2-(2-methylphenyl)-3,4-dihydronaphthalen-1-yl][4-[2-(1-piperidinyl)ethoxy]phenyl]methanol

[2-(3-methylphenyl)-3,4-dihydro-6-methoxynaphthalen-1-yl][4-[2-(1-piperidinyl)ethoxy]phenyl]methanol

[2-(2-chloro-4-fluorophenyl)-3,4-dihydro-6-methoxynaphthalen-1-yl][4-[2-(1-piperidinyl)ethoxy]phenyl]methanol

[2-(2,4-di-methoxyphenyl)-3,4-dihydro-6-methoxynaphthalen-1-yl][4-[2-(1-piperidinyl)ethoxy]phenyl]methanol

[2-(3-methoxyphenyl)3,4-dihydro-6-methoxynaphthalen-1-yl][4-[2-(1-pyrolidinyl)ethoxy]phenyl]methanol

[2-(3-methoxyphenyl)3,4-dihydro-6-methoxynaphthalen-1-yl][4-[3-(1-piperidinyl)propoxy]phenyl]methanol

[2-(3-methoxy-4-fluorophenyl)-3,4-dihydro-6-methoxynaphthalen-1-yl][4-[2-(1-piperidinyl)ethoxy]phenyl]methanol

[2-(2-methyl-3-methoxyphenyl)-3,4-dihydro-6-methoxynaphthalen-1-yl][4-[2-(1-piperidinyl)ethoxy]phenyl]methanol

[2-(3-chloro-4-methoxyphenyl)-3,4-dihydro-6-methoxynaphthalen-1-yl][4-[2-(1-piperidinyl)ethoxy]phenyl]methanol

[2-(3-methoxyphenyl)-3,4-dihydro-6-methoxynaphthalen-1-yl][4-[2-(1-hexamethylenimino)ethoxy]phenyl]methanol

[2-(3,4-di-methoxyphenyl)-3,4-dihydro-6-methoxynaphthalen-1-yl][4-[2-(1-piperidinyl)ethoxy]phenyl]methanol

[2-(3-hydroxyphenyl)-3,4-dihydro-6-hydroxynaphthalen-1-yl][4-[2-(1-piperidinyl)ethoxy]phenyl]methanol

[2-(3-hydroxyphenyl)-3,4-dihydronaphthalen-1-yl][4-[2-(1-piperidinyl)ethoxy]phenyl]methanol and the like.

A compound of formula III$^a$, wherein $R^{3a}$ is not an oxygen-bearing function, may be converted to a compound of formula I$^a$ by protonation of the secondary alcohol with a strong acid, and subsequent, spontanous elimination of water and aromatization of the cyclohexene ring. This sequence is further illustrated in Scheme V, below.

Scheme V

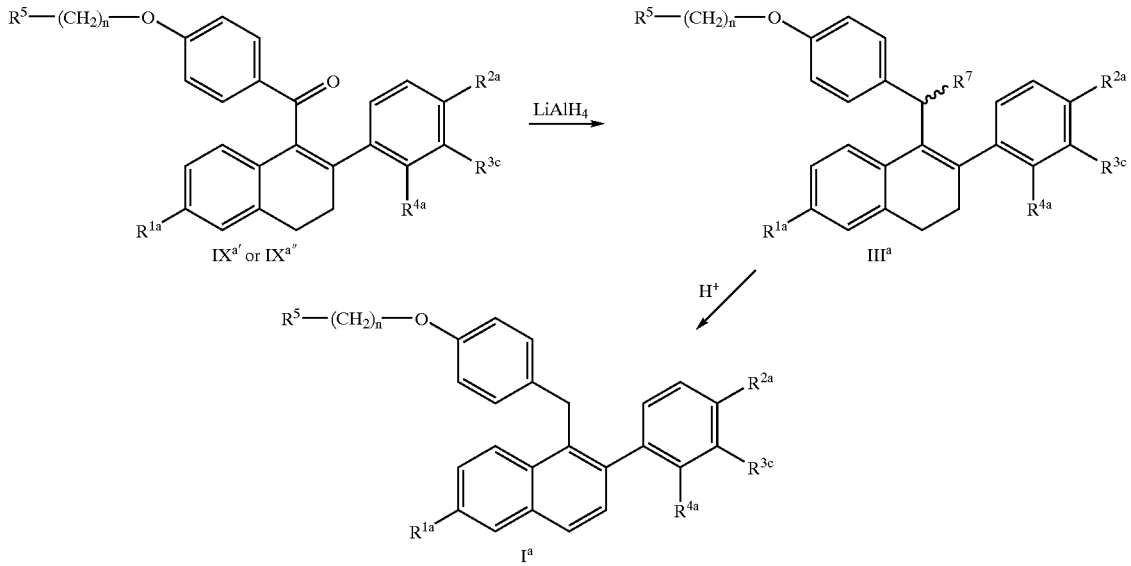

wherein:

R$^{1a}$, R$^{2a}$, R$^{4a}$, R$^5$, and n have their previous meanings,

R$^7$ is —OH, and

R$^{3c}$ is —H, —Cl, —F, or —C$_1$–C$_4$ alkyl, with the proviso that both R$^{3c}$ and R$^{4a}$ are not both hydrogen.

The chemistry for this transformation of III$^a$ to I$^a$ is revealed in the references cited, supra. Briefly, a compound of formula III$^a$ is dissolved in an inert solvent, such as, alkyl esters, alchols, ether, THF, hydrocarbons, halogenated hydrocarbons, and the like, preferred solvents would-be ethylacetate or ethanol. This solution is treated with a molar excess of a strong acid, usually dissolved in the same solvent as the reactant. A two to twenty fold molar excess of the acid is preferred and hydrogen chloride is the preferred acid, other useful acids would be sulfuric, phosphoric, trifuoroacetic, toluenesulfonic, and the like. The reaction may be run at a wide variety of temperatures from –20 to 50° C., conveniently ambient temperature is preferred. The reaction is complete almost immediately; however, usually several hours are allowed to elapse. The product may be isolated by standard purification procedures, such as, chromatography using silica gel and eluting solvents such as mixtures of CHCl$_3$ and MeOH or EtOAc-hexanes, and the like.

The compounds of formula I$^a$ would include, but are not limited to:

[2-(2-methoxyphenyl)-6-methoxynaphthalen-1-yl][4-[2-(1-piperidinyl)ethoxy]phenyl]methane

[2-(2,4-di-methoxyphenyl)-6-methoxynaphthalen-1-yl][4-[2-(1-piperidinyl)ethoxy]phenyl]methane

[2-(2-methoxyphenyl)naphthalen-1-yl][4-[2-(1-piperidinyl)ethoxy]phenyl]methane

[2-(3-fluorophenyl)-6-methoxynaphthalen-1-yl][4-[2-(1-piperidinyl)ethoxy]phenyl]methane

[2-(3-chlorophenyl)-6-methoxynaphthalen-1-yl][4-[2-(1-pyroidinyl)ethoxy]phenyl]methane

[2-(3-fluoro-4-methoxyphenyl)-6-methoxynaphthalen-1-yl][4-[3-(1-piperidinyl)propoxy]phenyl]methane

[2-(2-methox-3-chlorophenyl)-6-methoxynaphthalen-1-yl][4-[2-(N,N-dimethylamino)ethoxy]phenyl]methane

[2-(2-ethyl-4-chlorophenyl)-6-methoxynaphthalen-1-yl][4-[2-(1-piperidinyl)ethoxy]phenyl]methane

[2-(2-methoxyphenyl)-6-methoxynaphthalen-1-yl][4-[2-(1-hexamethyleneimino)ethoxy]phenyl]methane

[2-(3-ethyl-4-methoxyphenyl)-6-methoxynaphthalen-1-yl][4-[2-(1-piperidinyl)ethoxy]phenyl]methane

[2-(2-methyl-4-chlorophenyl)naphthalen-1-yl][4-[3-(1-(2-methylpyrolidinyl))propoxy]phenyl]methane

[2-(2,4-di-methoxyphenyl)-6-methoxynaphthalen-1-yl][4-[2-(1-(3,3-dimethylpyrolidinyl))ethoxy]phenyl]methane

[2-(2-methyl-4-methoxyphenyl)naphthalen-1-yl][4-[2-(1-pyrolidinyl)ethoxy]phenyl]methane

[2-(2-methyl-3-ethylphenyl)-6-methoxynaphthalen-1-yl][4-[2-(1-piperidinyl)ethoxy]phenyl]methane

[2-(2-ethylphenyl)-6-methoxynaphthalen-1-yl][4-[3-(1-piperidinyl)propoxy]phenyl]methane

[2-(2-methoxy-3-chloro-4-fluorophenyl)-6-methoxynaphthalen-1-yl][4-[2-(1-piperidinyl)ethoxy]phenyl]methane

[2-(2-ethyl-3-chlorophenyl)-6-methoxynaphthalen-1-yl][4-[2-(1-(3-methylpyrolidinyl))ethoxy]phenyl]methane

[2-(2-ethylphenyl)-naphthalen-1-yl][4-[2-(4-morpholino)ethoxy]phenyl]methane

[2-(2-methylphenyl)-6-methoxynaphthalen-1-yl][4-[3-(4-morpholino)propoxy]phenyl]methane and the like.

As mentioned previously, the synthetic route outlined above may be employed for the preparation of the compounds of the current invention with the exception of those with an oxygen function on the 3-position of the pendant phenyl moiety. Attempts at using the dehydration and elimination reaction on compounds of formula III, when R$^{3a}$ is an oxygen-containing fuction, leads to the formation of undesired products. The preparation of compounds of formula I$^b$, as well as those of formula I$^a$, is outlined in Scheme VI, below.

Scheme VI

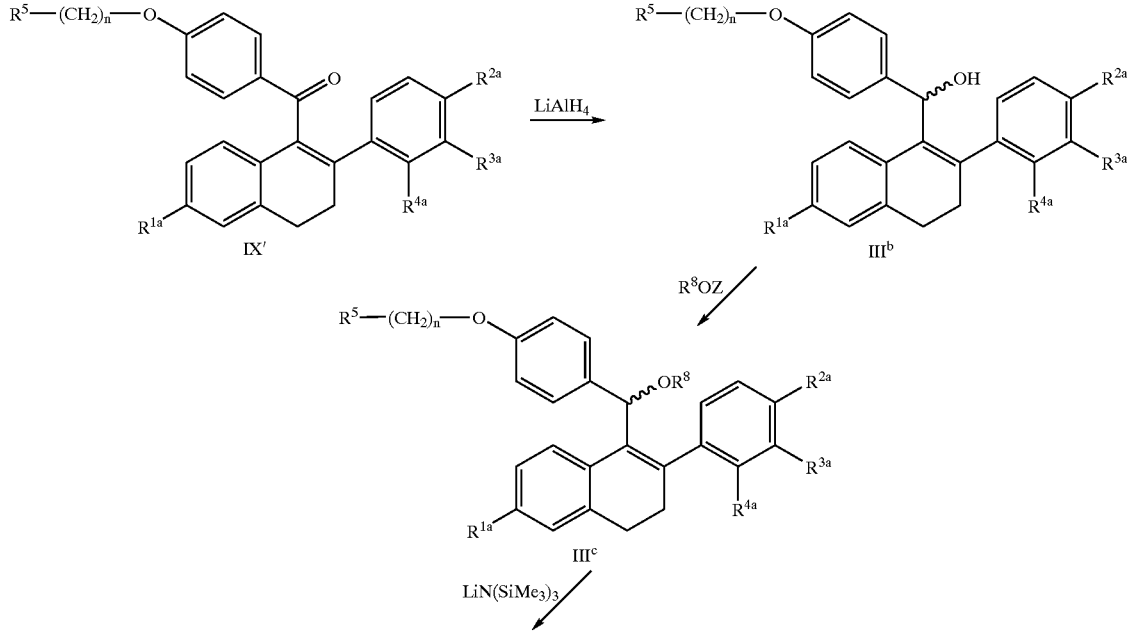

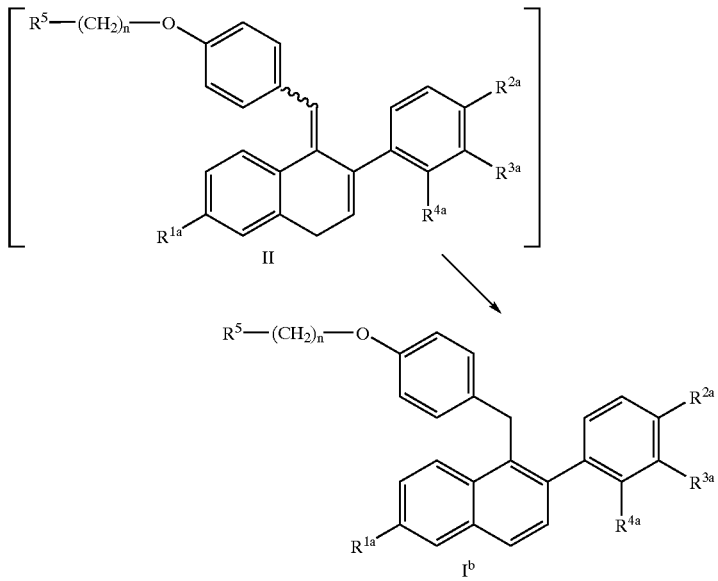

wherein:
$R^{1a}$, $R^{2a}$, $R^{3a}$, $R^{4a}$, $R^5$, $R^8$, and n have their previous meanings and provisions; and Z is a sulfonic acid activating moiety, including —Cl, —Br, —N³, or homo/mixed anhydrides.

The preferred starting material for this synthetic sequence is a compound of formula IX', where any hydroxy functions are protected. Although compounds of formula IX" may be used, it is not recommended, due to the reactive nature of the hydroxyls with $R^8OZ$.

Compounds of formula IX' are reduced to their corresponding secondary alcohols (III$^b$) in exactly the same manner as discussed, supra. Compounds of formula III$^b$ are sulfonylated to the compounds of formula III$^c$, in order to convert the secondary alcohol to a better leaving group for the subsequent elimination step. This sulfonylation is accomplished by reacting III$^b$ with $R^8OZ$ in the presence of an acid scavenger. Examples of suitable $R^8OZ$ compounds would include mesyl chloride, tosyl chloride, propansulfonyl bromide, phenylsulfonyl azide, p-methoxybenzosulfonyl anhydride, ethylsulfonyl-methylsulfonyl anhydride, and the like, preferred is $CH_3SO_2Cl$, methanesulfonyl chloride or mesyl chloride. The acid scavenger may be organic or inorganic bases, such as triethylamine, pyridine, lutidines, $Na_2CO_3$, $Cs_2CO_3$, $NaHCO_3$, and the like, with a preferred base being triethylamine. These reactions are run in inert solvents, such as ether, THF, hydrocarbons, halogenated hydrocarbons, and the like, a preferred solvent would be THF. Further, these reactions may be run at a variety of temperatures from 0° to 50° C. and are usually complete within one to six hours. The compounds of formula III$^c$ may be isolated or more conveniently used directly in the next synthetic step. The compounds of formula III$^c$ are novel and useful for the preparation of the compounds of the current invention (I). The compounds of formula III$^c$ would include, but not be limited to:

[2-(3-methoxyphenyl)-3,4-dihydro-6-methoxynaphthalen-1-yl][4-[2-(1-piperidinyl)ethoxy]phenyl]methanoxy methanesulfonate

[2-(3-methoxyphenyl)-3,4-dihydronaphthalen-1-yl][4-[2-(1-piperidinyl)ethoxy]phenyl]methanoxy methanesulfonate

[2-(2-methoxyphenyl)-3,4-dihydro-6-methoxynaphthalen-1-yl][4-[2-(1-piperidinyl)ethoxy]phenyl]methanoxy tosylate

[2-(2-methylphenyl)-3,4-dihydronaphthalen-1-yl][4-[2-(1-piperidinyl)ethoxy]phenyl]methanoxy n-butanesulfonate

[2-(3-methylphenyl)-3,4-dihydro-6-methoxynaphthalen-1-yl][4-[2-(1-piperidinyl)ethoxy]phenyl]methanoxy methansulfonate

[2-(2-chloro-4-fluorophenyl)-3,4-dihydro-6-methoxynaphthalen-1-yl][4-[2-(1-piperidinyl)ethoxy]phenyl]methanoxy benzosulfonate

[2-(2,4-di-methoxyphenyl)-3,4-dihydro-6-methoxynaphthalen-1-yl][4-[2-(1-piperidinyl)ethoxy]phenyl]methanoxy propanesulfonate

[2-(3-methoxyphenyl)3,4-dihydro-6-methoxynaphthalen-1-yl][4-[2-(1-pyrrolidinyl)ethoxy]phenyl]methanoxy methanesulfonate

[2-(3-methoxyphenyl)3,4-dihydro-6-methoxynaphthalen-1-yl][4-[3-(1-piperidinyl)propoxy]phenyl]methanoxy tosylate

[2-(3-methoxy-4-fluorophenyl)-3,4-dihydro-6-methoxynaphthalen-1-yl][4-[2-(1-piperidinyl)ethoxy]phenyl]methanoxy methansulfonate

[2-(2-methyl-3-methoxyphenyl)-3,4-dihydro-6-methoxynaphthalen-1-yl][4-[2-(1-piperidinyl)ethoxy]phenyl]methanoxy n-butansulfonate

[2-(3-chloro-4-methoxyphenyl)-3,4-dihydro-6-methoxynaphthalen-1-yl][4-[2-(1-piperidinyl)ethoxy]phenyl]methanoxy hexanesulfonate

[2-(3-methoxyphenyl)-3,4-dihydro-6-methoxynaphthalen-1-yl][4-[2-(1-hexamethylenimino)ethoxy]phenyl]methanoxy ethanesulfonate

[2-(3,4-di-methoxyphenyl)-3,4-dihydro-6-methoxynaphthalen-1-yl][4-[2-(1-piperidinyl)ethoxy]phenyl]methanoxy methanesulfonate

[2-(3-hydroxyphenyl)-3,4-dihydro-6-hydroxynaphthalen-1-yl][4-[2-(1-piperidinyl)ethoxy]phenyl]methanoxy benzosulfonate

[2-(3-hydroxyphenyl)-3,4-dihydronaphthalen-1-yl][4-[2-(1-piperidinyl)ethoxy]phenyl]methanoxy methanesulfonate and the like.

The reaction sequence continues by the conversion of compounds of III$^c$ to the compounds of formula II by a hydrogen abstraction on the 3 position of the dihydronaphthalene, electron shift, and elimination of the OR$^8$ group. The compounds of formula II are inherently unstable and will thermally rearrange to the compounds of formula I$^b$. Thus, the compounds of formula II are usually not isolated, but allowed to rearrange to the compounds of the current invention. However, if desired the compounds of formula II may be isolated at low temperatures, especially if temperatures are <–50° C.

The hydrogen abstraction is accomplished by use of a strong base, for example, a hydride-NaH, LiH, and the like, an alkali metal amide-NaNH$_2$, NaNEt$_2$, and the like, or alkali metal silico-ammoniate-LiN(SiMe$_3$)$_3$, and the like. A preferred reagent would be LiN(SiMe$_3$)$_3$. This reaction is carried out in an inert solvent, such as, ether, THF, hydrocarbons, and the like. THF is the preferred solvent. The reaction may be carried out at a variety of temperatures 0° to 50° C., most coveniently it is run at ambient temperature. The reaction is complete in two to sixteen hours. As stated before, the compounds of formula II are inherently unstable and will isomerize to the compounds of the current invention (I$^b$) in about sixteen hours at ambient temperature in THF. If desired the compounds of formula II may be kept at low temperature (<–50° C.) and in an inert atmosphere, such as nitrogen.

The compounds of formula II are novel and useful in the synthesis of the compounds of the current invention. Compounds of formula II would include, but not be limited to:

[2-(3-methoxyphenyl)-4-hydro-6-methoxynaphthalen-1-ene-yl][4-[2-(1-piperidinyl)ethoxy]phenyl]methine

[2-(2-methoxyphenyl)-4-hydro-6-methoxynaphthalen-1-ene-yl][4-[2-(1-piperidinyl)ethoxy]phenyl]methine

[2-(3,4-di-methoxyphenyl)-4-hydro-6-methoxynaphthalen-1-ene-yl][4-[2-(1-piperidinyl)ethoxy]phenyl]methine

[2-(3-fluorophenyl)-4-hydro-6-methoxynaphthalen-1-ene-yl][4-[2-(1-piperidinyl)ethoxy]phenyl]methine

[2-(3-methoxyphenyl)-4-hydro-naphthalen-1-ene-yl][4-[2-(1-piperidinyl)ethoxy]phenyl]methine

[2-(3-methoxyphenyl)-4-hydro-6-methoxynaphthalen-1-ene-yl][4-[2-(1-pyrolidinyl)ethoxy]phenyl]methine

[2-(3-methoxyphenyl)-4-hydro-6-methoxynaphthalen-1-ene-yl][4-[3-(1-piperidinyl)propoxy]phenyl]methine

[2-(3-methoxyphenyl)-4-hydro-6-methoxynaphthalen-1-ene-yl][4-[2-(N,N-diethylamino)ethoxy]phenyl]methine

[2-(2-methyl-3-methoxyphenyl)-4-hydro-6-methoxynaphthalen-1-ene-yl][4-[2-(1-piperidinyl)ethoxy]phenyl]methine

[2-(3-methoxy-4-chlorophenyl)-4-hydro-6-methoxynaphthalen-1-ene-yl][4-[2-(1-hexamethyleneimino)ethoxy]phenyl]methine and the like.

It should be noted that the compounds of I$^a$ are a subset of I$^b$ and thus the chemistry described in Scheme VI will also enable the preparation of I$^a$ compounds. Compounds of formula I$^b$ would include, but not be limited to:

[2-(3-methoxyphenyl)-6-methoxynaphthalen-1-yl][4-[2-(1-piperidinyl)ethoxy]phenyl]methane

[2-(3,4-di-methoxyphenyl)-6-methoxynaphthalen-1-yl][4-[2-(1-piperidinyl)ethoxy]phenyl]methane

[2-(2,3-di-methoxyphenyl)naphthalen-1-yl][4-[2-(1-piperidinyl)ethoxy]phenyl]methane

[2-(3-methoxy-4-fluorophenyl)-6-methoxynaphthalen-1-yl][4-[2-(1-piperidinyl)ethoxy]phenyl]methane

[2-(3-methoxy-4-chlorophenyl)-6-methoxynaphthalen-1-yl][4-[2-(1-pyroidinyl)ethoxy]phenyl]methane

[2-(3-fluoro-4-methoxyphenyl)-6-methoxynaphthalen-1-yl][4-[3-(1-piperidinyl)propoxy]phenyl]methane

[2-(3-methoxyphenyl)-6-methoxynaphthalen-1-yl][4-[2-(N,N-dimethylamino)ethoxy]phenyl]methane

[2-(2-ethyl-3-methoxyphenyl)-6-methoxynaphthalen-1-yl][4-[2-(1-piperidinyl)ethoxy]phenyl]methane

[2-(3-methoxyphenyl)-6-methoxynaphthalen-1-yl][4-[2-(1-hexamethyleneimino)ethoxy]phenyl]methane

[2-(3-methoxy-4-methylphenyl)-6-methoxynaphthalen-1-yl][4-[2-(1-piperidinyl)ethoxy]phenyl]methane

[2-(3-methoxy-4-chlorophenyl)naphthalen-1-yl][4-[3-(1-(2-methylpyrolidinyl))propoxy]phenyl]methane

[2-(2,3,4-tri-methoxyphenyl)-6-methoxynaphthalen-1-yl][4-[2-(1-(3,3-dimethylpyrolidinyl))ethoxy]phenyl]methane

[2-(3-methoxy-4-methoxyphenyl)naphthalen-1-yl][4-[2-(1-pyrolidinyl)ethoxy]phenyl]methane

[2-(2-methyl-3-methoxyphenyl)-6-methoxynaphthalen-1-yl][4-[3-(1-piperidinyl)propoxy]phenyl]methane

[2-(2-ethyl-3-methoxyphenyl)-6-methoxynaphthalen-1-yl][4-[3-(1-piperidinyl)propoxy]phenyl]methane

[2-(2-methyl-3-methoxy-4-fluorophenyl)-6-methoxynaphthalen-1-yl][4-[2-(1-piperidinyl)ethoxy]phenyl]methane

[2-(3-methoxyphenyl)-6-methoxynaphthalen-1-yl][4-[2-(1-(3-methylpyrolidinyl))ethoxy]phenyl]methane

[2-(2-ethyl-3-methoxyphenyl)-naphthalen-1-yl][4-[2-(4-morpholino)ethoxy]phenyl]methane

[2-(2-methyl-3-methoxyphenyl)-6-methoxynaphthalen-1-yl][4-[3-(4-morpholino)propoxy]phenyl]methane and the like.

Other compounds of the current invention (I), wherein R$^{1-4}$ are acyl, sulfonyl, or carbonate derivatives, for example, compounds of formula Id, are prepared from the hydroxyl compounds I$^c$. Compounds I$^c$ are prepared from either I$^a$ or I$^b$ by removing the hydroxy protecting group R$^6$. This chemistry is further illustrated in Scheme VII, below.

Scheme VII

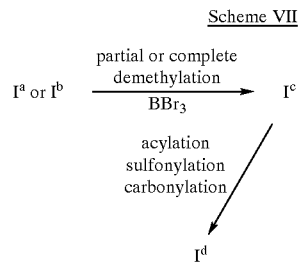

Deprotection of the hydroxy functions to form the compounds I$^c$ is discussed in the references cited, supra. Most germane to the removal of the preferred protecting group (wherein R$^6$ is methyl) of the current invention is the reaction of I$^a$ or b with a Lewis acid, for example, BBr$_3$, AlCl$_3$, BCl$_3$, and the like. This reaction is run in an inert solvent, such as ether, THF, halogenated hydrocarbons, and the like, and is run at temperatures from 0° to 50° C. for one to twenty-four hours. Preferred conditions for the present invention would the use of BBr$_3$ in CH$_2$Cl$_2$ at reflux for three hours. (For a detailed description of this process, see the examples, below.)

The compounds of formula I$^c$ would include, but are not limited to:

[2-(3-hydroxyphenyl)-6-hydroxynaphthalen-1-yl][4-[2-(1-piperidinyl)ethoxy]phenyl]methane

[2-(3-hydroxyphenyl)naphthalen-1-yl][4-[2-(1-piperidinyl)ethoxy]phenyl]methane

[2-(3-hydroxyphenyl)-6-hydroxynaphthalen-1-yl][4-[2-(1-pyroidinyl)ethoxy]phenyl]methane

[2-(3-hydroxyphenyl)-6-hydroxynaphthalen-1-yl][4-[3-(1-piperidinyl)propoxy]phenyl]methane

[2-(3-methoxyphenyl)-6-hydroxynaphthalen-1-yl][4-[2-(1-piperidinyl)ethoxy]phenyl]methane

[2-(3-methoxyphenyl)-6-hydroxynaphthalen-1-yl][4-[2-(1-pyrolidinyl)ethoxy]phenyl]methane

[2-(3-methoxyphenyl)-6-hydroxynaphthalen-1-yl][4-[2-(1-piperidinyl)ethoxy]phenyl]methane

[2-(3,4-di-methoxyphenyl)-6-methoxynaphthalen-1-yl][4-[2-(1-piperidinyl)ethoxy]phenyl]methane

[2-(2,3-di-methoxyphenyl)naphthalen-1-yl][4-[2-(4-morpholino)ethoxy]phenyl]methane

[2-(3-methoxyphenyl)-6-hydroxynaphthalen-1-yl][4-[2-(1-hexamethyleneimino)ethoxy]phenyl]methane

[2-(3-methoxy-4-fluorophenyl)-6-hydroxynaphthalen-1-yl][4-[2-(1-piperidinyl)ethoxy]phenyl]methane

[2-(3-hydroxy-4-chlorophenyl)-6-methoxynaphthalen-1-yl][4-[2-(1-pyroidinyl)ethoxy]phenyl]methane

[2-(3-fluoro-4-hydroxyphenyl)-6-hydroxynaphthalen-1-yl][4-[3-(1-piperidinyl)propoxy]phenyl]methane

[2-(3-methoxyphenyl)-6-hydroxynaphthalen-1-yl][4-[2-(N,N-dimethylamino)ethoxy]phenyl]methane

[2-(2-ethyl-3-hydroxyphenyl)-6-hydroxynaphthalen-1-yl][4-[2-(1-piperidinyl)ethoxy]phenyl]methane

[2-(3-hydroxyphenyl)-6-methoxynaphthalen-1-yl][4-[2-(1-hexamethyleneimino)ethoxy]phenyl]methane

[2-(3-hydroxy-4-methylphenyl)-6-hydroxynaphthalen-1-yl][4-[2-(1-piperidinyl)ethoxy]phenyl]methane

[2-(3-hydroxy-4-chlorophenyl)naphthalen-1-yl][4-[3-(1-(2-methylpyrolidinyl))propoxy]phenyl]methane

[2-(2,3,4-tri-hydroxyphenyl)-6-hydroxynaphthalen-1-yl][4-[2-(1-(3,3-dimethylpyrolidinyl))ethoxy]phenyl]methane

[2-(3-hydroxy-4-methoxyphenyl)naphthalen-1-yl][4-[2-(1-pyrolidinyl)ethoxy]phenyl]methane

[2-(2-methyl-3-hydroxyphenyl)-6-hydroxynaphthalen-1-yl][4-[3-(1-piperidinyl)propoxy]phenyl]methane

[2-(2-ethyl-3-methoxyphenyl)-6-hydroxynaphthalen-1-yl][4-[3-(1-piperidinyl)propoxy]phenyl]methane

[2-(2-methyl-3-hydroxy-4-fluorophenyl)-6-hydroxynaphthalen-1-yl][4-[2-(1-piperidinyl)ethoxy]phenyl]methane

[2-(3-hydroxyphenyl)-6-hydroxynaphthalen-1-yl][4-[2-(1-(3-methylpyrolidinyl))ethoxy]phenyl]methane

[2-(2-ethyl-3-methoxyphenyl)-naphthalen-1-yl][4-[2-(4-morpholino)ethoxy]phenyl]methane

[2-(2-methyl-3-methoxyphenyl)-6-hydroxynaphthalen-1-yl][4-[3-(4-morpholino)propoxy]phenyl]methane

[2-(2-hydroxyphenyl)-6-hydroxynaphthalen-1-yl][4-[2-(1-piperidinyl)ethoxy]phenyl]methane

[2-(2,4-di-hydroxyphenyl)-6-hydroxynaphthalen-1-yl][4-[2-(1-piperidinyl)ethoxy]phenyl]methane

[2-(2-hydroxyphenyl)naphthalen-1-yl][4-[2-(1-piperidinyl)ethoxy]phenyl]methane

[2-(3-fluorophenyl)-6-hydroxynaphthalen-1-yl][4-[2-(1-piperidinyl)ethoxy]phenyl]methane

[2-(3-chlorophenyl)-6-hydroxynaphthalen-1-yl][4-[2-(1-pyroidinyl)ethoxy]phenyl]methane

[2-(3-fluoro-4-methoxyphenyl)-6-hydroxynaphthalen-1-yl][4-[3-(1-piperidinyl)propoxy]phenyl]methane

[2-(2-hydroxy-3-chlorophenyl)-6-hydroxynaphthalen-1-yl][4-[2-(N,N-dimethylamino)ethoxy]phenyl]methane

[2-(2-ethyl-4-chlorophenyl)-6-hydroxynaphthalen-1-yl][4-[2-(1-piperidinyl)ethoxy]phenyl]methane

[2-(2-hydroxyphenyl)-6-hydroxynaphthalen-1-yl][4-[2-(1-hexamethyleneimino)ethoxy]phenyl]methane

[2-(3-ethyl-4-hydroxyphenyl)-6-methoxynaphthalen-1-yl][4-[2-(1-piperidinyl)ethoxy]phenyl]methane

[2-(2-methyl-3-hydroxy-4-chlorophenyl)naphthalen-1-yl][4-[3-(1-(2-methylpyrolidinyl))propoxy]phenyl]methane

[2-(2,4-di-methoxyphenyl)-6-hydroxynaphthalen-1-yl][4-[2-(1-(3,3-dimethylpyrolidinyl))ethoxy]phenyl]methane

[2-(2-methyl-4-hydroxyphenyl)naphthalen-1-yl][4-[2-(1-(pyrolidinyl)ethoxy]phenyl)methane

[2-(2-methyl-3-ethylphenyl)-6-hydroxynaphthalen-1-y][4-[2-(1-piperidinyl)ethoxy]phenyl]methane

[2-(2-ethylphenyl)-6-hydroxynaphthalen-1-yl][4-[3-(1-piperidinyl)propoxy]phenyl]methane

[2-(2-hydroxy-3-chloro-4-fluorophenyl)-6-hydroxynaphthalen-1-yl][4-[2-(1-piperidinyl)ethoxy]phenyl]methane

[2-(2-ethyl-3-chlorophenyl)-6-hydroxynaphthalen-1-yl][4-[2-(1-(3-methylpyrolidinyl))ethoxy]phenyl]methane

[2-(2-ethylphenyl-4-hydroxy)-naphthalen-1-yl][4-[2-(4-morpholino)ethoxy]phenyl]methane

[2-(2-methylphenyl)-6-hydroxynaphthalen-1-yl][4-[3-(4-morpholino)propoxy]phenyl]methane and the like.

Acyl and sulfonyl compounds (I$^d$) of formula I are prepared by replacing 2',3', 4' and/or 6-position hydroxy moieties of I$^c$, when present, with a moiety of the formula —O—CO—(C$_1$–C$_6$ alkyl), —OCAr, where Ar is phenyl or substituted phenyl, —O(CO)O(C$_1$–C$_6$ alkyl) or —O—SO$_2$—(C$_2$–C$_6$ alkyl) via well known procedures. Such methods are described in U.S. Pat. Nos. 5,393,763 and 5,482,949, the disclosures of which are herein incorporated by reference.

For example, when an —O—CO(C$_1$–C$_6$ alkyl) group is desired, a mono-, di-, tri, or tetra-hydroxy compound of formula Ia is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam, et al., *Tetrahedron*, 36:2409–2433 (1980).

The present reactions are carried out at moderate temperatures, in the range from about −25° C. to about 100°

C., frequently under an inert atmosphere such as nitrogen gas. However, ambient temperature is usually adequate for the reaction to run.

Acylation of a 2',3', 4' and/or 6-position hydroxy groups also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^2$, $R^3$, and/or $R^4$ groups of formula $I^d$ compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, *Bull. Chem. Soc.* Japan, 38: 1979 (1965), and *Chem. Ber.*, 788 and 2024 (1970).

Each of the above techniques which provide —O—CO—($C_1$–$C_6$ alkyl) moieties are carried out in solvents as discussed above. Those techniques which do not produce an acid product in the course of the reaction, of course, do not call for the use of an acid scavenger in the reaction mixture.

When a formula $I^d$ compound is desired in which the 2',3', 4' and/or 6-position hydroxy group of a formula $I^c$ compound is converted to a group of the formula —O—$SO_2$—($C_4$–$C_6$ alkyl), the mono-, di-, tri, or tetra-hydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The hydroxy compounds also can be reacted with the appropriate sulfonic anhydride or mixed sulfonic anhydrides.

Such reactions are carried out under conditions such as were explained above in the discussion of the reaction with acid. halides.

The compounds of formula $I^d$ would include, but not be limited to:

[2-(3-acetoxyphenyl)-6-acetoxynaphthalen-1-yl][4-[2-(1-piperidinyl)ethoxy]phenyl]methane

[2-(3-benzoyloxyphenyl)-6-benzoyloxynaphthalen-1-yl][4-[2-(1-piperidinyl)ethoxy]phenyl]methane

[2-(3-n-butylsulfonyloxyphenyl)-6-n-butylsulfonyloxynaphthalen-1-yl][4-[2-(1-piperidinyl)ethoxy]phenyl]methane

[2-(3-methoxyphenyl)-6-acetoxynaphthalen-1-yl][4-[2-(1-piperidinyl)ethoxy]phenyl]methane

[2-(3-methoxyphenyl)-6-benzoyloxynaphthalen-1-yl][4-[2-(1-piperidinyl)ethoxy]phenyl]methane

[2-(3-methoxyphenyl)-6-benzoyloxynaphthalen-1-yl][4-[2-(1-pyroidinyl)ethoxy]phenyl]methane

[2-(2-acetoxyphenyl)-6-acetoxynaphthalen-1-yl][4-[2-(1-piperidinyl)ethoxy]phenyl]methane

[2-(3-acetoxyphenyl)naphthalen-1-yl][4-[2-(1-piperidinyl)ethoxy]phenyl]methane

[2-(3-acetoxy-4fluorophenyl)-6-acetoxynaphthalen-1-yl][4-[2-(1-piperidinyl)ethoxy]phenyl]methane

[2-(2-benzoyloxy-3-chlorophenyl)-6-benzoyloxynaphthalen-1-yl][4-[2-(1-piperidinyl)ethoxy]phenyl]methane and the like.

Together, the compounds of formula $I^a$, $I^b$, $I^c$, and $I^d$ comprise the genus of the compounds of formula I, which are useful for the pharmacological methods described herein.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

The pharmaceutically acceptable acid addition salts are typically formed by reacting a compound of formula with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The term "solvate" represents an aggregate that comprises one or more molecules of the solute, such as a formula I compound, with one or more molecules of solvent. The term "solvate" represents an aggregate that comprises one or more molecules of the solute, such as a formula I compound, with one or more molecules of solvent.

The present invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the present invention which is capable of inhibiting, alleviating, ameliorating, treating, or preventing further symptoms in mammals, including humans, suffering from estrogen deprivation, for example, menopause or ovariectomy, or inappropriate estrogen stimulation such as uterine fibrosis or endometriosis, or suffering from aortal smooth muscle cell profileration or restenosis. In the case of estrogen-dependent cancers, the term "effective amount" means the amount of compound of the present invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy, normally for at least six months.

The present invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed infra. The present invention contemplates and encompasses such maladies although not specified by name.

Compounds of the current invention may also be used in conjunction with other mixed estrogen agonists/antagonists, especially those which demonstrate increased detrimental stimulation of uterine tissue, such as, for example, tamoxifen, droloxifene, nafoxidene, or clomiphene.

As a further embodiment of the invention, the compounds of formula I may be administered along with an effective amount of an additional therapeutic agent, including but not limited to estrogen, progestin, other benzothiophene compounds including raloxifene, bisphosphonate compounds such as alendronate and tiludronate, parathyroid hormone (PTH), including truncated and/or recombinant forms of PTH such as, for example, PTH (1–34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-α-ethynyl estradiol (0.01–0.03 mg/day), mestranol (0.05–0.15 mg/day), and conjugated estrogenic hormones such as Premarin® (Wyeth-Ayerst; 0.2–2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera® (Upjohn; 2.5–10 mg/day), norethylnodrel (1.0–10.0 mg/day), and norethindrone (0.5–2.0 mg/day). A preferred estrogen-based compound is Premarin®, and norethylnodrel and norethindrone are referred progestin-based agents. The method of administration of each estrogen- and progestin-based agent is consistent with that known in the art.

The formulations which follow are given for purposes of illustration and are not intended to be limiting in any way. The total active ingredients in such formulations comprises from 0.1% to 99.9% by weight of the formulation. The term "active ingredient" means a compound of formula I.

| Formulation 1: Gelatin Capsules | |
| --- | --- |
| Ingredient | Quantity (mg/capsule) |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

| Formulation 2: Tablets | |
| --- | --- |
| Ingredient | Quantity (mg/tablet) |
| Active Ingredient | 2.5–1000 |
| Starch | 10–50 |
| Cellulose, microcrystalline | 10–20 |

-continued

Formulation 2: Tablets

| Ingredient | Quantity (mg/tablet) |
| --- | --- |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.25 |
| Ethanol | 29.75 |
| Propellant 22 | 70.00 |
| (Chlorodifluoromethane) | |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension
Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following examples and preparations are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

NMR data for the following Examples were generated on a GE 300 MHz NMR instrument, and anhydrous d-6 DMSO was used as the solvent unless otherwise indicated.

Preparation 1

1-(4-Methoxybenzoyl)-3,4-dihydro-6-methoxynaphthalenyl-2-Diphenyl Phosphoric Acid Ester

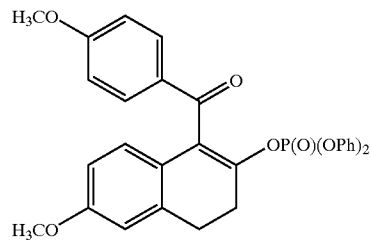

To a solution of 1-(4-methoxybenzoyl)-2-hydroxy-3,4-dihydro-6-methoxynaphthalene2(1H)-naphthalenone (1.50 g, 0.0048 mol) at 50° C. under $N_2$ in 15 mL $CH_2Cl_2$ was added diphenylchlorophosphate (1.36 g, 0.0051 mol) and 4-dimethylaminopyridine (5 mg). Triethylamine (0.514 g, 0.0051 mol) in $CH_2Cl_2$ (20 mL) as then added dropwise over 10 min, while keeping the reaction temperature below 5° C., The resulting mixture was stirred overnight, and then it as poured over brine and ice and the crude product was extracted by EtOAc (50 mL). The organic layer was washed well with brine, dried over anhydrous $K_2CO_3$, and evaporated to obtain 2.92 g of a yellow oil. Silica gel chromatography which utilized 10% EtOAc in toluene gave the desired product as a yellow oil, 2.17 g (83%) This material gave a strong peak in its field desorption mass spectrum at M/e 542 and was essentially a single component by NMR spectroscopy. Nevertheless, it failed to crystallize and did not give an acceptable combustion analysis for carbon. Anal.

($C_{31}H_{27}PO_7$) calcd C, 68.63; H, 5.02, O, 12.96. Found: C, 65.37; H, 4.89; O, 13.26. $^1$H NMR (CDCl$_3$) δ 7.91 (d, J=8.8 Hz, 2H), 7.20–6.97 (m, 9H), 6.95–6.73 (m, 5H), 6.58 (dd, J=8.5 Hz, J=2.4 Hz, 1H), 3.83 (s, 3H), 3.75 (s, 3H), 3.07 (t, J=7.8 Hz, 2H), 2.88 (t, J=7.8 Hz, 2H); MS (FD) m/e 542 (M+).

Preparation 2

[2-(3-Methoxyphenyl)-3,4-dihydro-6-methoxynaphthalen-1-yl][4-methoxyphenyl]methanone

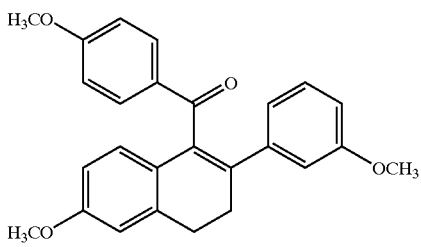

Sodium hydride (60% in mineral oil, 5.4 g, 0.135 mol) was suspended in anhydrous THF (80 mL) under a nitrogen atmosphere and the mixture was cooled to 5° C. in an ice bath. A solution consisting of 1-(4-methoxybenzoyl)-3,4-dihydro-6-methoxynaphthalenyl-2-diphenyl phosphoric acid ester (38.0 g, 0.122 mol) and diphenyl chlorophosphate (36.3 g, 28.0 mL, 0.135 mol) in THF (150 mL) was added at a rate so that the temperature of the reaction mixture remained below 10° C. Following the initially rapid evolution of hydrogen gas, the reaction mixture was stirred for 2 hr with continued cooling from the ice bath. Analysis of a small sample by TLC (SiO$_2$, Toluene-EtOAc 9-1) showed essentially quantitative formation of the enolphosphate intermediate. The reaction mixture was maintained near 0° C. and 3-methoxyphenyl magnesium bromide (250 mL of a 0.74 M solution in THF, 0.185 mol) was added by cannula over approximately 5 min. The resulting mixture was stirred at 0° C. for 2 hour, and then it was allowed to warm to 25° C. overnight. By TLC analysis, loss of enolphosphate had accompanied-the formation of a major product which migrated at high Rf. The reaction was worked up by pouring it over a large excess of iced NH$_4$Cl solution, and the crude product was extracted with with ethyl acetate. The organic extracts were washed with brine and dried over anhydrous sodium sulfate. After filtration and removal of the solvents, a brown oil was obtained. The oil was purified by chromatography over silica gel which employed a hexane to chloroform gradient. Pooling and concentration of appropriate fractions gave an amber oil which amounted to 40.3 g (83%): $^1$H NMR (CDCl$_3$) δ 7.85 (d, J=8.6 Hz, 2H)7.10–7.0 (m, 1H), 6.90–6.70 (m, 6H), 6.70–6.60 (m, 2H), 3.80 (s, 6H), 3.67 (s, 3H), 3.10–2.90 (m, 2H), 2.90–2.70 (m, 2H); MS (FD) m/e 400 (M+); Anal. Calc'd. for $C_{26}H_{24}O_4$: C, 77.98; H, 6,04; N, 0.00. Found: C, 77.49; H, 6.20; N, 0.00.

Preparation 3

2-Diphenylphosphoroyloxy-3,4-dihydro-6-methoxynaphthalen-1-yl][1-[4-[2-(1-piperidinyl)ethoxy]phenyl]methanone

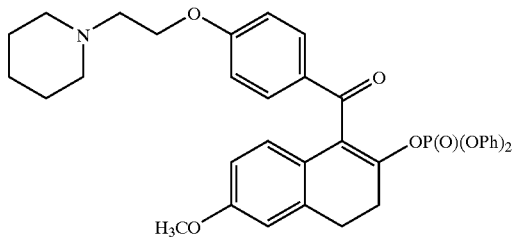

In a manner similar to that used in Preparation 1, the title compound was prepared as a yellow oil.

$^1$H NMR (CDCl$_3$) δ 7.85 (d, J=8.7 Hz, 2H), 7.39–6.92 (m, 9H), 6.92–6.69 (m, 5H), 6.57 (dd, J=8.5 Hz, J=2.4 Hz, 1H), 4.03 (t, J=5.9 Hz, 2H), 3.77 (s, 3H), 3.07 (t, J=8.1 Hz, 2H), 2.89 (t, J=8.1 Hz, 2H), 2.78 (t, J=7.2, 2H), 2.62–2.42 (m, 4H), 1.77–1.55 (m, 4H), 1.55–1.37 (m, 2H); MS (FD) m/e 639 (M+).

Preparation 4

[2-(3-Methoxyphenyl)-3,4-dihydro-6-methoxynaphthale-1-yl][4-[2-(1-piperidinyl)ethoxy]phenyl]methanone Hydrochloride

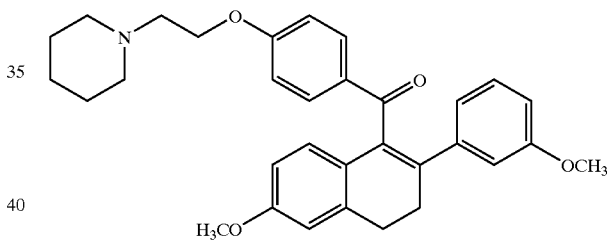

Sodium hydride (60% in mineral oil, 2.68 g, 0.067 mol) was suspended in anhydrous THF (300 mL) under a nitrogen atmosphere and the suspension was cooled to 5° C. in an ice bath. A solution consisting of [2-hydroxy-3,4-dihydro-6-methoxynaphthalen-1-yl][1-[4-[2-(1-piperidinyl)ethoxy]phenyl]methanone(26.0 g, 0.0638 mol) in a minimum of THF was added dropwise and after the evolution of hydrogen subsided, the mixture was kept cooled and stirred for an hour to complete formation of the enolate. With continued cooling, diphenyl chlorophosphate (17.1 g, 13.2 mL, 0.0638 mol) in THF (75 mL) was added at a rate so that the temperature of the reaction mixture remained below 10° C. Following the completion of the addition, the reaction mixture was allowed to warm to room temperature while stirring was continued. Analysis of a small sample by TLC (SiO$_2$, Toluene-EtOAc 9-1) showed essentially quantitative formation of the enol phosphate intermediate. The reaction mixture was maintained near 50° C. and 3-methoxyphenyl magnesium bromide (150 mL of a 0.64 M solution in THF, 0.096 mol) was added by cannula. The resulting mixture was stirred at 0° C. for 1 hour, and then it was allowed to warm to 250 C. and stirred for one hour longer. The reaction was kept cooled and carefully quenched by gradual addition of 50 mL of 1N sulfuric acid. After adjusting the pH to 7.0, most of the THF was removed under reduced pressure. The aqueous residue was distributed between water and chloroform. The organic layer was washed with brine and dried over anhydrous sodium sulfate. Concentration provided an oil which was purified by chromatography over silica gel which utilized a gradient of chloroform to 95:5 chloroform:methanol to elute the product. Appropriate fractions provided 36 gms of the crude free base which was practically identical to the free base product of Example 2. The free base was dissolved in methanol and treated with an excess of 5N HCl solution, then concentrated to dryness. The residue was recrystallized from methanol-ethyl acetate to provide 27.8 g (82%) of the desired hydrochloride salt: $^1$H NMR (DMSO-$d_6$) δ 10.09 (bs, 1H), 7.76 (d, J=8.7 Hz, 1H), 7.11–7.02 (m, 2H), 6.94 (d, J=8.8 Hz, 1H), 6.86 (d, J=1.2 Hz, 1H), 6.81–6.72 (m, 2H), 6.66 (dd, J=8.2 Hz, 2.5, 1H), 6.61 (d, J=3.1 Hz, 1H), 4.37 (t, J=4.6 Hz, 2H), 3.69 (s, 3H), 3.57 (s, 3H), 3.01–2.82 (m, 4H), 2.78–2.63(m, 2H), 1.81–1.58 (m, 5H), 1.31 (m, 1H); MS (FD) m/e 497 (M+; loss of HCl); Anal. Calc'd. for Anal. Calc'd. for $C_{32}H_{36}ClNO_4$: C, 71.96; H, 6.79; N. 2.62. Found: C, 71.69; H, 6.77; N, 2.48.

Preparation 5

[2-(3-Methoxyphenyl)-6-methoxynaphthalen-1-yl][4-methoxyphenyl]methanone

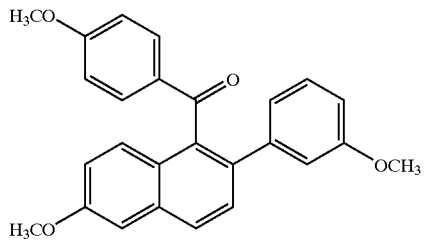

A solution of [2-(3-methoxy phenyl)-3,4-dihydro-6-methoxynaphthaleny-1-yl][4-methoxyphenyl]methanone (14.0 g, 35.0 mmol) was dissolved in anhydrous dioxane (400 mL) under an atmosphere of nitrogen. 2,3-dichloro-5,6-dicyano-1,4-benzoquinone (DDQ, 7.0 g, 31 mmol) was added and the solution was refluxed for 16 hours. The reaction mixture was allowed to cool to ambient temperature and the solid dihydroquinone byproduct (8.8 gm) was removed by filtration and discarded. The filtrate was concentrated to dryness and the residue was purified by silica gel chromatography with chloroform as the isocratic elution solvent. Appropriate fractions gave 13.1 g, (94%) of the desired product as an oil. Although the oil contained some minor impurities, it was used without additional purification. $^1$H NMR (CDCl$_3$) δ 7.88 (d, J=8.6 Hz, 1H), 7.71–7.54 (m, 4H), 7.21 (d, J=2.6 Hz, 1H), 7.18–7.05 (m, 2H), 6.99–6.89 (m, 2H), 6.78–6.70 (m, 3H), 3.94 (s, 3H), 3.78 (s, 3H), 3.69 (s, 3H); MS (FD) m/e 398 (M+); Anal. Calcd. for $C_{26}H_{22}O_4$: C, 78.37; H, 5.57. Found: C, 8.22; H, 5.83.

Preparation 6

[2-(3-Methoxyphenyl)-3,4-dihydro-6-methoxynaphthalen-1-yl][4-hydroxyphenyl]methanone

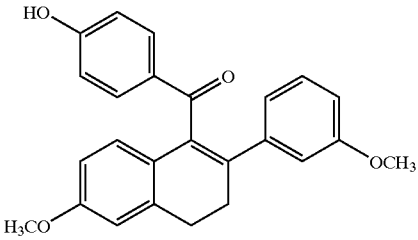

To EtSH (12.5 g, 14.9 mL. 0.20 mol) in anhydrous ethyl ether (300 mL) at −78° C. under a dry nitrogen atmosphere in a 1 L single neck RB flask was added slowly via syringe 1.6M n-BuLi (113 mL, 0.180 mol) over 1 hour. After addition was complete, the ether was removed under vacuum and a solution of [2-(3-methoxyphenyl)-3,4-dihydro-6-methoxynaphthalen-1-yl][4-methoxyphenyl]methanone, (24.0 g, 0.065 mol) in anhydrous DMF (150 mL) was added. The reaction mixture was heated at 70–80° C. for 2.5 hours and then at 65° C. for 20 hr. TLC analysis (SiO$_2$, Toluene-EtOAc 9-1) showed the starting material to be nearly gone. Two spots were present at lower Rf. These were attributed to the desired product and the corresponding diphenol (lowest spot). The reaction mixture was allowed to cool and was then poured into 500 mL iced 1N HCl solution. The crude product was extracted into EtOAc. The EtOAc phase was washed with saturated aq. NaCl solution, dried over anhydrous MgSO$_4$, and evaporated to a yellow oil. The product was purified by chromatography over silica gel using a gradient consisting of chloroform changing linearly 95:5 chloroform: methanol. Following evaporation of the appropriate fractions, a yellow oil was obtained which was recrystallized from ethyl ether to yield 21.3 g, (54%) of the desired product, mp 197–8° C. $^1$H NMR (CDCl$_3$) δ 7.76 (d, J=8.6 Hz, 2H), 7.10–7.00 (m, 1H), 6.90–6.70 (m, 4H), 6.70–6.60 (m, 4H), 6.07 (bs, 1H), 3.78 (s, 3H), 3.62 (s, 3H), 3.10–2.90 (m, 2H), 2.90–2.70 (m, 21H); MS (FD) m/e 386 (M+); Anal. Calc'd. for $C_{25}H_{22}O_4$: C, 77.70; H. 5.74. Found: C, 77.45; H, 5.66.

Preparation 7

[2-(3-Methoxyphenyl)-6-methoxynaphthalen-1-yl](4-hydroxyphenyl)methanone

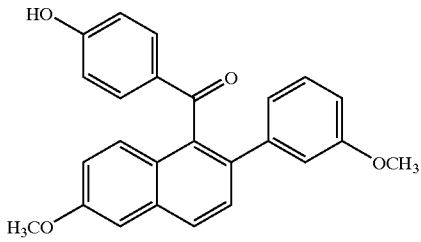

The above compound was prepared in an analogous manner as Preparation 6. The title compound was isolated as a tan solid, 6.3 g (50%), mp 158–9° C. $^1$H NMR (CDCl$_3$) δ 7.86 (d, J=8.4 Hz, 1H), 7.63–7.49 (m, 4H), 7.20 (d, J=2.6 Hz, 1H), 7.15–7.05 (m, 2H), 6.95–6.86 (m, 2H), 6.70 (d, J=8.0 Hz, 1H), 6.61 (d, J=8.8 Hz, 2H), 6.32 (bs, 1H), 3.93 (s, 3H), 3.63 (s, 3H); MS (FD) m/e 384 (M+); Anal. Calcd. for $C_{25}H_{20}O_4$: C, 78.11; H, 5.24. Found: C, 78.36; H, 5.27.

Preparation 8

[2-(3-Methoxyphenyl)-3,4-dihydro-6-methoxynaphthalen-1-yl][4-[2-(1-piperidinyl)ethoxy]phenyl]methanone (Alternate Synthesis)

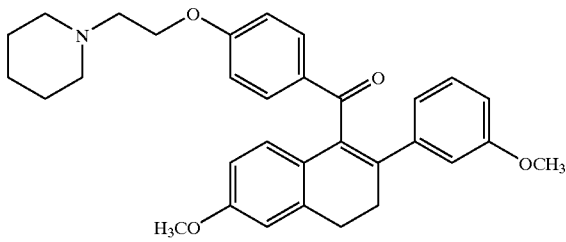

[2-(3-methoxyphenyl)-3,4-dihydro-6-methoxynaphthalen-1-yl][4-hydroxyphenyl]methanone, (3.5 g, 9.0 mmol), anhydrous $K_2CO_3$ (6.25 g, 45 mmol), N-2-chloroethylpiperidine hydrochloride (1.75 g, 9.5 mmol, Aldrich Chem. Co.) 10 mg of KI, and anhydrous DMF (150 mL) were combined under a nitrogen atmosphere and the resulting mixture was stirred at room temperature for 16 hr. The DMF was removed under reduced pressure and the residue was distributed into water and ethyl acetate. The organic layer was separated, washed with brine and dried over anhydrous sodium sulfate. After concentration to an oil, the product was purified by column chromatography over silica gel using a gradient from chloroform to 95:5 chloroform:methanol. The appropriate fractions gave, on evaporation of the solvent and vacuum drying of the residue at 80° C. overnight, an oil which weighed 3.1 g. (69%). $^1$H NMR (CDCl$_3$) δ 7.80 (d, J=9.0 Hz, 2H), 7.10–7.00 (m, 1H), 6.90–6.70 (m, 6H), 6.70–6.68 (m, 2H), 4.09 (t, J=5.9 Hz, 2H), 3.78 (s, 3H), 3.65 (s, 3H), 3.02 (t, J=8.1 Hz, 2H), 2.90–2.70 (m, 4H), 2.60–2.40 (m, 3H), 1.70–1.50 (m, 5H), 1.50–1.01 (m, 2H); MS (FD) m/e 497 (M+); Anal. Calc'd. for $C_{32}H_{35}NO_4$: C, 77.24; H, 7.09; N, 2.82. Found: C, 77.05; H, 7.19; N, 3.05.

Preparation 9

[2-(3-Methoxyphenyl)6-methoxynaphthalen-1-yl][4-[2-(1-piperidinyl)ethoxy]phenyl]methanone Hydrochloride

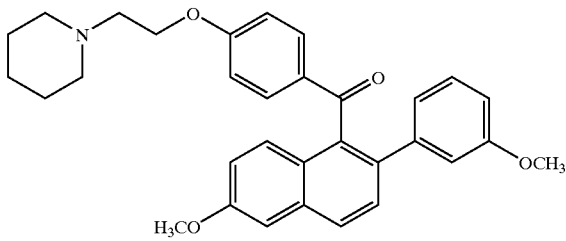

The above compound was prepared in an analogous manner to that of Preparation 8, and isolated as the hydrochloride salt. White solid, 6.95 g (80%), mp 91–2° C. $^1$H NMR (DMSO-d$_6$) δ 10.24 (bs, 1H), 8.01 (d, J=8.6 Hz, 1H), 7.61–7.52 (m, 4H), 7.46 (d, J=2.4 Hz, 1H), 7.20–7.11 (m, 2H), 6.97–6.81 (m, 4H), 6.76 (dd, J=8.6, J=2.4, 1H), 4.41–4.31 (m, 2H), 3.87 (s, 3H), 3.61 (s, 3H), 3.52–3.33 (m, 4H), 3.01–2.80 (m, 2H), 1.80–1.58 (m, 5H), 1.31 (m, 1H),; MS (FD) m/e 496 (MH+ of free base); Anal. Calc'd. for $C_{32}H_{34}ClNO_4$: C, 72.24; H, 6.44; N, 2.63. Found: C, 72.53; H, 6.56; N, 2.66.

Preparation 10

[2-(3-Methoxyphenyl)-6-methoxynaphthalen-1-yl][4-[2-(1-piperidinyl)ethoxy]phenyl]methanol A solution of 6.7 g (13.4 mmol) of [2-(3-methoxyphenyl)-6-methoxynaphthalen-1-yl][4-[2-(1-piperidinyl)ethoxy]phenyl]methanone in 200 mL of THF was prepared and 1.02 g (27 mmol) of LiAlH$_4$ was added. The reaction was allowed to proceed at ambient temperature under a nitrogen atmosphere for three hours. The reaction was quenched with the addition of 10 mL of 5 N NaOH. The mixture was extracted with ether and the ether layer was washed with brine. The ether solution was dried with anhydrous Na$_2$SO$_4$ and evaporated to dryness. This yielded 6.6 g of the title compound a tan amorphous powder. PMR: Consistent with the proposed structure.

Preparation 11

[2-(3-Methoxyphenyl)-6-methoxynaphthalen-1-yl][4-[2-(1-piperidinyl)ethoxy]phenyl]methanol Methanesulfonate A solution was prepared of 6.5 g (13 mmol) of [2-(3-methoxyphenyl)-6-methoxynaphthalen-1-yl][4-[2-(1-piperidinyl)ethoxy]phenyl]methanol in 200 mL of anhydrous THF. To the solution was added 10 mL (8 mmol) of triethylamine 2.4 mL (3.6 g, 30 mmol) of mathanesulfonyl chloride. The reaction was allowed to proceed for two hours at ambient temperature. The formation of the title compound was confirmed by tlc analysis. In this preparation, the title product was not isolated, but used in Example 1, below.

Example 1

[2-(3-Methoxyphenyl)-6-methoxynaphthalen-1-yl][4-[2-(1-piperidinyl)ethoxy]phenyl]methane Hydrochloride The reaction product from Preparation 11, supra, was treated with 104 mL of 1 M LiN(SiMe$_3$)$_3$ in THF (31 mmol). The reaction was allowed to proceed at ambient temperature for eighteen hours. The reaction was quenched with 100 mL of water and 100 mL of brine was added. The reaction mixture was extracted with CHCl$_3$ and organic layer was dried with Na$_2$SO$_4$ and evaporated to dryness. The residue was further purified by by chromatography on a silica gel column eluted with a linear gradient beginning-with CHCl$_3$ and ending with CHCl$_3$:MeOH (49:1) (v/v). The desired fractions were determined by tlc, combined, and evaporated to dryness. The residue was dissolved in MeOH and excess 1 N HCl was added. The solvent were removed by evaporation and the product crystallized from EtOAc. This yielded 300 mg of the title compound as a white crystalline solid.

H$^1$ NMR (DMSO-d$_6$) δ 10.22 (bvs, 1H), 7.78 (d, J=8.5 Hz, 1H), 7.72 (d, J=9.4 Hz, 1H), 7.42–7.27 (m, 3H), 7.06 (d, J=8.5 Hz, 1H), 6.98–6.73 (m, 7H), 4.27 (s, 2H), 4.38–4.19 (m, 2H), 3.83 (s, 3H), 3.61 (s, 3H), 3.52–3.30 (m, 4H), 3.02–2.82 (m, 2H), 1.80–1.59 (m, 5H), 1.40–1.22 (m, 1H). MS: m/e=481 (M-HCl) FD; EA: Calc. for $C_{32}H_{35}NO_3$-HCl: C, 74.19; H, 7.00; N, 2.70; Found: C, 73.91; H, 7.25; N, 2.84.

Example 2

[2-(3-Hydroxyphenyl)-6-hydroxynaphthalen-1-yl][4-[2-(1-piperidinyl)ethoxy]phenyl]methane Hydrochloride A solution was prepared of [2-(3-methoxyphenyl)-6-methoxynaphthalen-1-yl][4-[2-(1-piperidinyl)ethoxy]phenyl]methane hydrochloride (1 g, 1.9 mmol) in 50 mL of $CHCl_3$ and to 0° C. To this solution was added 0.72 mL (7.7 mmol) of $BBr_3$. The reaction was allowed to proceed for three hours before quenching with aqueous $NaHCO_3$ and the product extracted with THF. The THF solution was dried with $Na_2SO_4$ and evaporated to dryness. The crude product was purified by chromatography on a silica gel column eluted with $THF:CHCl_3$ (1:1) (v/v). The free base was converted to its hydrochloride salt by addition of excess 1N HCl. The product (340 mg) was isolated as a white amorphous solid.

$H^1$ NMR (DMSO-$d_6$) δ 9.94 (bvs, 1H), 9.74 (s, 1H), 9.51 (s, 1H), 7.71 (d, J=9.5 Hz, 1H), 7.66 (d, J=8.0 Hz, 1H), 7.50 (d, J=7.5 Hz, 1H), 7.21–7.13 (m, 3H), 7.01 (dd, J=9.0 Hz, J=2.5 Hz, 1H), 6.92 (d, J=9.0 Hz, 2H), 6.84 (d, J=7.0 Hz, 2H), 7.78–6.68(m, 2H), 4.31 (s, 2H), 4.35–4.22 (m, 2H), 3.52–3.36 (m, 4H), 3.05–2.88 (m, 2H), 1.85–1.60 (m, 5H), 1.45–1.29 (m, 1H). MS: m/e=454 (M-HCl) FD; IR: (KBr) 3190, 2949, 2649, 2541, 1609, 1509, 1473,1444, 1388, 1283, 1237, 1179, 1157, 956 $cm^{-1}$; EA: Calc. for $C_{30}H_{31}NO_3$-HCl: C, 73.53; H, 6.58; N, 2.86; Found: C, 73.26; H, 6.35; N, 3.06.

The following discussions further illustrate methods of use for the compounds of formula I in experimental models or in clinical studies. These examples are for the purposes of illustration and are not meant to be limiting in any way.

A. Osteoporosis:

Experimental models of postmenopausal osteoporosis are known in the art. Germane to this invention is the ovariectomized rat model which is provided in U.S. Pat. No. 5,393,763. The compounds of formula I would be active in this model and would demonstrate an effective treatment or prevention of bone loss due to the deprivation of estrogen.

An additional demonstration of the method of treating or preventing osteoporosis due to estrogen deprivation would be as follows: One hundred patients would be chosen, who are healthy postmenopausal women, aged 45–60 and who would normally be considered candidates for estrogen replacement therapy. This includes women with an intact uterus, who have had a last menstrual period more than six months, but less than six years. Patients excluded for the study would be those who have taken estrogens, progestins, or corticosteroids six months prior to the study or who have ever taken bis-phosphonates.

Fifty women (test group) would receive 15–80 mg of a compound of formula I, for example, Formulation 1 (above), per day. The other fifty women (control group) would receive a matched placebo per day. Both groups would receive calcium carbonate tablets (648 mg) per day. The study is a double-blind design. Neither the investigators nor the patients would know to which group each patient is assigned.

A baseline examination of each patient includes quantitative measurement of urinary calcium, creatinine, hydroxyproline, and pyridinoline crosslinks. Blood samples are measured for serum levels of osteocalcin and bone-specific alkaline phosphatase. Baseline measurements would also include a uterine examination and bone mineral density determination by photon absorptiometry.

The study would continue for six months, and each the patients would be examined for changes in the above parameters. During the course of treatment, the patients in the treatment group would show a decreased change in the biochemical markers of bone resorption as compared to the control group. Also, the treatment group would show little or no decrease in bone mineral density compared to the control group. Both groups would have similar uterine histology, indicating the compounds of formula I have little or no utrotrophic effects.

B. Hyperlipidemia:

Experimental models of postmenopausal hyperlipidemia are known in the art. Germane to this invention is the ovariectomized rat model which is detailed in U.S. Pat. No. 5,464,845. Data presented in Table 1 show comparative results among ovariectomized rats, rats treated with 17-α-ethynyl estradiol ($EE_2$), and rats treated with certain compounds of this invention. Although $EE_2$ caused a decrease in serum cholesterol when orally administered at 0.1 mg/kg/day, it also exerted a stimulatory effect on the uterus so that $EE_2$ uterine weight was substantially greater than the uterine weight of the ovariectomized animals. This uterine response to estrogen is well recognized in the art.

Not only did the compounds of the present invention reduce serum cholesterol compared to the ovariectomized animals, but the uterine weight was increased to lesser extent than those given $EE_2$. Compared to estrogenic compounds known in the art, the benefit of serum cholesterol reduction while lessening the effect on uterine weight is unusual and desirable.

As expressed in the data below, estrogenicity also was assessed by evaluating the response of eosinophil infiltration into the uterus. The compounds of this invention did not cause as large an increase in the number of eosinophils observed in the stromal layer of the ovariectomized, rat uteri. $EE_2$ caused a substantial and expected increase in eosinophil infiltration.

The data presented in Table 1 reflect the response per treatment group.

In accordance with the above procedures, compounds of the present invention and ethynyl estradiol ($EE_2$) in 20% hydroxypropyl β-cyclodextrin are orally administered to test animals.

TABLE

| Compound | Dose mg/kg)[a] | Uterine Wt. (% Inc.)[b] | Uterine EPO (Vmax)[c] | Serum cholesterol (% Dec.)[d] |
|---|---|---|---|---|
| $EE_2$[e] | 0.1 | 128.0* | 133.8* | 87.5* |
| Ex. 1 | 0.1 | 30.9* | 7.5 | 68.4* |
|  | 1 | 31.6* | 5.4 | 74.1* |
|  | 10 | 37.2* | 6.0 | 65.0* |
| Ex. 2 | 0.1 | 37.6* | 4.8 | 6.6 |
|  | 1.0 | 44.7* | 4.8 | 28.6 |
|  | 10.0 | 28.1* | 4.8 | 46.6* |

[a]mg/kg PO
[b]Uterine Weight % increase versus the ovariectomized controls
[c]Eosinophil peroxidase, $V$max
[d]Serum cholesterol decrease versus ovariectomized controls
[e]17-α-Ethynyl-estradiol An additional demonstration of the method of treating hyperlipidemia due to estrogen deprivation would be as follows: One hundred patients would be chosen, who are healthy postmenopausal women, aged 45–60, and who would normally be considered candidates for estrogen replacement therapy. This would include women with an intact uterus, who have not had a menstrual period for more than six months, but less than six years. Patients excluded for the study would be those who have taken estrogens, progestins, or corticosteroids.

Fifty women (test group) would receive 15–80 mg of a compound of formula I, for example, using Formulation 1, per day. The other fifty women (control group) would receive a matched placebo per day. The study would be a double-blind design. Neither the investigators nor the patients would know to which group each patient is assigned.

A baseline examination of each patient would include serum determination of cholesterol and tri-glyceride levels. At the end of the study period (six months), each patient would have their serum lipid profile taken. Analysis of the data would confirm a lowering of the serum lipids, for example, cholesterol and/or tri-glycerides, in the test group versus the control.

MCF-7 Proliferation Assay

MCF-7 breast adenocarcinoma cells (ATCC HTB 22) were maintained in MEM (minimal essential medium, phenol red-free, Sigma, St. Louis, Mo.) supplimented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mm}, non-essential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca++/Mg++ free HBSS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 370° C. in a 5% $CO_2$ humidified incubator, microcultures were pulsed with tritiated thymidine (1 uCi/well) for 4 hours. Cultures were terminated by freezing at −700° C. for 24 hours followed by thawing and harvesting of microcultures using a Skatron Semiautomatic Cell Harvester. Samples were counted by liquid scintillation using a Wallac BetaPlace β counter. The compounds of formula I are active and potent in inhibiting the tumor cell growth, for example, the compound of Example 1 has an $IC_{50}$ of 0.1 nM.

We claim:

1. A compound of formula I $$R^5-(CH_2)_n-O-\text{[structure]}-R^2,R^3,R^4,R^1$$

I wherein $R^1$ is —OH, —O($C_1$-$C_4$ alkyl), —OCO($C_1$-$C_6$ alkyl), —O—CO—O($C_1$-$C_6$ alkyl), —O—CO—Ar, —O—$SO_2$($C_2$-$C_6$ alkyl), —O—CO—OAr where Ar is optionally substituted phenyl;

$R^2$ is —H;

$R^3$ and $R^4$ are, independently, —H, —OH, —O($C_1$-$C_4$ alkyl), —OCO($C_1$-$C_6$ alkyl), —O—CO—O($C_1$-$C_6$ alkyl), —O—CO—Ar, —O—$SO_2$($C_2$-$C_6$ alkyl), —O—CO—OAr where Ar is optionally substituted phenyl, with the proviso that $R^3$ and $R^4$ are not both hydrogen;

$R^5$ is 1-piperidinyl, 1-pyrrolidinyl, methyl-1-pyrrolidinyl, dimethyl-1-pyrrolidinyl, 4-morpholino, dimethylamino, diethylamino, diisopropylamino or 1-hexamethyleneimino; and n is 2 or 3; or a pharmaceutically acceptable salt thereof.

2. A compound according to claim 1 wherein $R^3$ is methoxy.

3. A compound according to claim 1 wherein $R^3$ is hydroxy.

4. A compound according to claim 2 wherein $R^1$ is methoxy.

5. A compound according to claim 3 wherein $R^1$ is hydroxy.

6. A compound according to claim 1 wherein n is two.

7. A compound of formula II $$R^5-(CH_2)_n-O-\text{[structure]}-R^{2a},R^{3a},R^{4a},R^{1a}$$

II wherein $R^{1a}$ is —H or —$OR^6$ in which $R^6$ is a hydroxy protecting group;

$R^{2a}$, $R^{3a}$, and $R^{4a}$ are, independently, —H, —Cl, —F, $C_1$-$C_4$ alkyl, —$OR^6$ in which $R^6$ is a hydroxy protecting group;

$R^5$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino;

n is 2 or 3;

and further, wherein said compound is in the Z— or E— stereoisomeric form.

8. A compound according to claim 7 wherein $R^6$ is methyl.

9. A compound according to claim 8 wherein $R^{3a}$ is methoxy.

10. A compound according to claim 9 wherein $R^{1a}$ is methoxy.

11. A pharmaceutically acceptable formulation comprising an effective amount of a compound of claim 1 and pharmaceutically acceptable excipients, carriers, or diluents.

12. A method for inhibiting bone loss or bone resorption comprising administering to a patient in need of such treatment an effective amount of a compound of claim 1, or a pharmaceutically acceptable salt or solvate thereof.

13. The method according to claim 12 wherein said bone loss or bone resorption is due to menopause or ovariectomy.

14. A method of lowering serum cholesterol comprising administering to a patient in need thereof an effective amount of a compound of claim 1, or a pharmaceutically acceptable salt or solvate thereof.

15. A method for treating estrogen dependent, cancer comprising administering to a patient in need thereof an effective amount of a compound of claim 1, or a pharmaceutically acceptable salt or solvate thereof.

16. A method according to claim 15 wherein the estrogen dependent cancer is breast cancer.

17. A method according to claim 15 wherein the estrogen dependent cancer is uterine cancer.

* * * * *